US008889414B2

(12) United States Patent
Alivisatos et al.

(10) Patent No.: US 8,889,414 B2
(45) Date of Patent: Nov. 18, 2014

(54) SEMICONDUCTOR NANOCRYSTAL-BASED PHAGOKINETIC TRACKING

(75) Inventors: A. Paul Alivisatos, Oakland, CA (US); Carolyn A. Larabell, Oakland, CA (US); Wolfgang J. Parak, Dachau (DE); Mark Le Gros, Oakland, CA (US); Rosanne Boudreau, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 10/285,187

(22) Filed: Oct. 30, 2002

(65) Prior Publication Data

US 2003/0113709 A1 Jun. 19, 2003

Related U.S. Application Data

(60) Provisional application No. 60/335,521, filed on Oct. 31, 2001.

(51) Int. Cl.
*C12N 5/00* (2006.01)
*G01N 33/58* (2006.01)
*B82Y 15/00* (2011.01)
*C12M 1/00* (2006.01)
*C12M 1/34* (2006.01)
*G01N 33/50* (2006.01)

(52) U.S. Cl.
CPC ............ *B82Y 15/00* (2013.01); *G01N 33/588* (2013.01); *C12M 23/20* (2013.01); *C12M 41/46* (2013.01); *G01N 33/5005* (2013.01); *Y10S 977/853* (2013.01)
USPC ................ 435/395; 435/325; 435/6; 436/43; 436/80; 977/853

(58) Field of Classification Search
CPC ............ A61K 49/0093; C12N 5/0006; C12N 2503/00; C12N 2533/00
USPC ....................................................... 435/325
See application file for complete search history.

(56) References Cited

U.S. PATENT DOCUMENTS

| | | | |
|---|---|---|---|
| 4,359,527 A | 11/1982 | Zetter | |
| 6,207,392 B1 | 3/2001 | Weiss et al. | |
| 6,238,874 B1 | 5/2001 | Jarnagin et al. | |
| 6,423,551 B1 | 7/2002 | Weiss et al. | |

OTHER PUBLICATIONS

Connolly L, Maxwell P., Image analysis of Transwell assays in the assessment of invasion by malignant cell lines. Br J Biomed Sci. 2002;59(1):11-4.
de la Monte SM, Lahousse SA, Carter J, Wands Jr., ATP luminescence-based motility-invasion assay, Biotechniques, Jul. 2002;33(1):98-100, 102, 104 passim.
Dong C, Slattery MJ, Rank BM, You J; In vitro characterization and micromechanics of tumor cell chemotactic protrusion, locomotion, and extravasation, Ann Biomed Eng. Mar. 2002;30(3):344-55.
Fong CJ, Sutkowski DM, Kozlowski JM, Lee C; Utilization of the Boyden chamber to further characterize in vitro migration and invasion of benign and malignant human prostatic epithelial cells; Invasion Metastasis. 1992;12(5-6):264-74.
Gildea JJ, Harding MA, Gulding KM, Theodorescu D; Transmembrane motility assay of transiently transfected cells by fluorescent cell counting and luciferase measurement; Biotechniques. Jul. 2000;29(1):81-6.
Grotendorst GR, Spectrophotometric assay for the quantitation of cell migration in the Boyden chamber chemotaxis assay, Methods Enzymol. 1987;147:144-52.
Heylen N, Baurain R, Remacle C, Trouet A ; Effect of MRC-5 fibroblast conditioned medium on breast cancer cell motility and invasion in vitro; Clin Exp Metastasis. Feb. 1998;16(2):193-203.
Imamura H, Takao S, Aikou T; A modified invasion-3-(4,5-dimethylthiazole-2-yl)-2,5-diphenyltetrazolium bromide assay for quantitating tumor cell invasion; Cancer Res. Jul. 1, 1994;54(13):3620-4.
Iwamoto Y, Sugioka Y ; Use of a reconstituted basement membrane to study the invasiveness of tumor cells; Adv Exp Med Biol. 1992;324:141-9.
Liu B, Rotenberg S, Mirkin M, Scanning electrochemical microscopy of living cells: different redox activities of nonmetastatic and metastatic human breast cells, Proc Natl Acad Sci U S A. Aug. 29, 2000;97(18):9855-60.
Maliakal JC; Quantitative high throughput endothelial cell migration and invasion assay system; Methods Enzymol. 2002;352:175-82.
McCafferty AC, Cree IA; Measurement of cell migration stimulated by interleukin 8: use of ATP chemiluminescence; Cytokine Jul. 1994; 6(4):450-3.
Mooradian DL, et al.; Effects of transforming growth factor-beta 1 on human pulmonary adenocarcinoma cell adhesion, motility, and invasion in vitro; J Natl Cancer Inst. Apr. 1, 1992;84(7):523-7.
Muir D, Sukhu L, Johnson J, Lahorra MA, Maria BL.. Quantitative methods for scoring cell migration and invasion in filter-based assays. Anal Biochem. Nov. 15, 1993;215(1):104-9.
Nam SW, Clair T, Schiffmann E, Liotta LA, Stracke ML. A sensitive screening assay for secreted motility-stimulating factors. Cell Motil Cytoskeleton. Aug. 2000;46(4):279-84
Okada T, Okuno H, Mitsui Y. A novel in vitro assay system for transendothelial tumor cell invasion: significance of E-selectin and alpha 3 integrin in the transendothelial invasion by HT1080 fibrosarcoma cells. Clin Exp Metastasis. Jul. 1994;12(4):305-14.
Partsch G, Schwarzer C. An indirect bioluminescence method for the quantitative measurement of polymorphonuclear cell chemotaxis. J Biolumin Chemilumin. Jul.-Sep. 1991;6(3):159-67.
Petty RD, Sutherland LA, Hunter EM, Cree IA. Comparison of MTT and ATP-based assays for the measurement of viable cell number. J Biolumin Chemilumin. Jan.-Feb. 1995;10(1):29-34.

(Continued)

*Primary Examiner* — Blaine Lankford
(74) *Attorney, Agent, or Firm* — Michelle Chew Wong; Lawrence Berkeley National Laboratory

(57) ABSTRACT

Methods for determining metabolic properties of living cells through the uptake of semiconductor nanocrystals by cells. Generally the methods require a layer of neutral or hydrophilic semiconductor nanocrystals and a layer of cells seeded onto a culture surface and changes in the layer of semiconductor nanocrystals are detected. The observed changes made to the layer of semiconductor nanocrystals can be correlated to such metabolic properties as metastatic potential, cell motility or migration.

22 Claims, 6 Drawing Sheets

(56) References Cited

OTHER PUBLICATIONS

Ricciardelli EJ, Persing JA, Romano JA, Morgan RF, Ogle RC. A rapid in vitro assay of cellular chemomigration in an epithelial carcinoma cell line. Plast Reconstr Surg. Dec. 1995;96(7):1689-93.
Saito K, Oku T, Ata N, Miyashiro H, Hattori M, Saiki I. A modified and convenient method for assessing tumor cell invasion and migration and its application to screening for inhibitors. Biol Pharm Bull. Apr. 1997;20(4):345-8.
Siegal GP, Wang MH, Rinehart CA Jr, Kennedy JW, Goodly LJ, Miller Y, Kaufman DG, Singh RK. Development of a novel human extracellular matrix for quantitation of the invasiveness of human cells. Cancer Lett. Apr. 30, 1993;69(2):123-32.
Sieuwerts AM, Klijn JG, Foekens JA. Assessment of the invasive potential of human gynecological tumor cell lines with the in vitro Boyden chamber assay: influences of the ability of cells to migrate through the filter membrane. Clin Exp Metastasis. Jan. 1997;15(1):53-62.
Silberman S, McGarvey T, Comrie E, Persky B, The influence of ethanol on cell membrane fluidity, migration, and invasion of murine melanoma cells, Exp Cell Res. Jul. 1990;189(1):64-8.
Simon N, Noel A, Foidart JM, Evaluation of in vitro reconstituted basement membrane assay to assess the invasiveness of tumor cells, Invasion Metastasis. 1992;12(3-4):156-67.
Sugihara K, Saito T, Okadome M, Sonoda K, Kobayashi H, Kamura T, Tsukamoto N, Nakano H. The promotion of invasion through the basement membrane of cervical carcinoma cells by fibronectin as a chemoattractant. Cancer Lett. May 16, 1994;79(2):167-73.
G. Albrecht-Buehler, "Phagokinetic tracks of 3T3 cells: parallels between the orientation of track segments and of cellular structures which contain actin or tubulin," Cell 12(2):333-9 (Oct. 1977).
G. Albrecht-Buehler, "The phagokinetic tracks of 3T3 cells," Cell 11(2):395-404(Jun. 1977).
Kömyei, et al., "Proliferative and migratory responses of astrocytes to in vitro injury," J. Neurosci. Res. 61, 421-429 (Aug. 2000).
R.R. Bürk, "A factor from a transformed cell line that affects cell migration," Proc Natl Acad Sci U S A. Feb. 1973;70(2):369-72.
S. Boyden, The Chemotactic Effect of Mixtures of Antibody and Antigen on Polymorphonuclear Leucocytes, J. Exp. Med. 115, 453-466 (1962).
Yao, et al., "Chemotaxis by a CNS Macrophage, the Microglia," J. Neurosci. Res. 27, 36-42 (1990).
Alivisatos AP, "Semiconductor Clusters, Nanocrystals, and Quantum Dots," Science Feb. 16, 1996; 271: 933-937.
Bruchez M Jr, Moronne M, Gin P, Weiss S, Alivisatos AP, Semiconductor nanocrystals as fluorescent biological labels, Science Sep. 25, 1998;281(5385):2013-6.
Chan WC, Nie S. Quantum Dot Bioconjugates for Ultrasensitive Nonisotopic Detection, Science Sep. 25, 1998;281(5385):2016-18.
Gerion, D.; Pinaud, F.; Williams, S. C.; Parak, W. J.; Zanchet, D.; Weiss, S.; Alivisatos, A. P.; Synthesis and Properties of Biocompatible Water-Soluble Silica-Coated CdSe/ZnS Semiconductor Quantum Dots, J. Phys. Chem. B. ; (Article); 2001; 105(37); 8861-8871.
Han M, Gao X, Su JZ, Nie S. Qunatum-dot-tagged microbeads for multiplexed optical coding of biomolecules. Nature Biotechnology 19:631-635 (Jul. 2001).
Manna L, Scher EC, Alivisatos AP. Synthesis of Soluble and Processable Rod-, Arrow-, Teardrop-, and Tetrapod-Shaped CdSe Nanocrystals. J.Am. Chem. Soc. Dec. 1, 2000; 122, 12700-12706.
Ostuni E, Chen CS, Ingber DE, Whitesides GM. Selective Deposition of Proteins and Cells in Arrays of Microwells. Langmuir Apr. 5, 2001; 17, 2828-2834.
Pathak S, Choi SK, Amheim N,Thompson ME. Hydroxylated Quantum Dots as Luminescent Probes for in Situ Hybridization. J. Am. Chem Soc. Apr. 7, 2001; 123,4103-4104.
Peng X, Manna L, Yang W, Wickham J, Scher E, Kadavanich A, Alivisatos AP. Shape control of CdSe nanocrystals. Nature 404, 59 (2000).
Squatrito R, Connor J, Buller R. Comparison of a Novel Redox Dye Cell Growth Assay to the ATP Bioluminescence Assay, Gynecologic Oncology 58, 101-105 (1995).

**MDA-MB-231 cells (green)
MCF 10A cells (red)**

SEMICONDUCTOR NANOCRYSTAL-BASED PHAGOKINETIC TRACKING

REFERENCE TO RELATED APPLICATIONS

This application claims priority to U.S. Provisional Patent Application No. 60/335,521 which was filed on Oct. 31, 2001 and is hereby incorporated by reference in its entirety.

STATEMENT OF GOVERNMENT SUPPORT

This invention was made during work partially supported by U.S. Department of Defense Award No. DAMD17-98-1-8182, DOD Advanced Research Projects Agency (DARPA) under Grant No. N00014-99-1-0728, and the National Institutes of Health under Grant No. 1 R01 RR-14891-01 through the U.S. Department of Energy under Contract No. DE-AC03-76SF00098. The government has certain rights in this invention.

BACKGROUND OF THE INVENTION

1. Field of the Invention

This invention generally relates to the field of semiconductor nanocrystals and to the field of cellular behavior and phenomena. More specifically, the invention provides a simple, reliable method of phagokinetic tracking using semiconductor nanocrystals. The invention has further application in the fields of observing live cell motility, migration, metastatic potential, cellular uptake and tracking cell lineage using semiconductor nanocrystals.

2. Description of the Related Art

Metastasis of cells is a major problem in cancer. Migration of cancerous cells leads to metastases and the formation of secondary tumors. Studies of chemotherapeutic agents depend upon cell motility assays. Current assays are cumbersome and prone to error, and require killing the cells which prevents further analyses.

The most direct method for observing cell motility currently is time lapse videos of cells in culture as described by Rajah, et al., *In vitro cell. Dev. Biol.—Animal* 34, 626-628 (1998). However, this method is restricted to measurements on just a few cells at a time, and therefore this approach is not widely used to make statistically significant studies of cell populations. Improved statistics can be obtained with the "scratched wound method" in which a region of the cell culture substrate is denuded of cells, and then the time scale for the filling of this "hole" is observed; unfortunately, the history of the cell migration paths are lost, and the analysis is complicated by subjective analysis of the complex and variable patterns of the cell motion that lead to hole filling. Környei, et al. *J. Neurosci. Res.* 61, 421-429 (2000); R. R. Bürk, *PNAS* 70, 369-371 (1981). A significant advance occurred with the development of the Boyden Chamber invasion assay, in which cells are seeded on one side of a membrane, and the rate of appearance of cells on the other side is monitored. Yao, et al., *J. Neurosci. Res.* 27, 36-42 (1990); S. Boyden, *J. Exp. Med.* 115, 453-466 (1962).

There are many commercially available versions of the Boyden Chamber technology. Many companies have modified the Chamber technology to use, for example, a stainless steel chamber (e.g. Neuro Probe BY312 BOYDEN CHAMBER, made by Neuro Probe, Inc., Gaithersburg, Md.) or creating chambers by clamping glass cover slips with silicon spacers (e.g. Hemogenix MODIFIED BOYDEN-CHAMBER #0729.000, made by HemoGenix LLC, Irmo, S.C.), or plastic microplates wherein each of the wells has a coated membrane on the bottom for cells to migrate through (e.g. QCM™ Quantitative Cell Migration Assay, made by CHEMICON International, Inc., Temecula, Calif.). The Boyden Chamber method is by far the most widely used, yet it is laborious; most protocols require that the cells be fixed or stained, and thus destroyed, and do not allow for real time variation of the external condition. Cells can be quantitated through various means such as by optical density or by fluorescence microscopy, but a significant number of cells are frequently lost during processing which decreases accuracy.

A recent cell motility assay has been developed and patented by Biometric Imaging, Inc. See Jarnagin, et al., U.S. Pat. No. 6,238,874. Jarnagin et al. describe an apparatus and method for assaying motility in response to a chemotaxic agent. The apparatus provides a chamber having two regions. The apparatus facilitates the establishment of a concentration gradient of the chemotactic agent which increases on progressing from the first region to the second region, also called the interrogation region. The individual cells are detected by comparing the distribution of detected, position-assigned cells in the interrogation region at two or more time intervals. The method of using this apparatus involves labeling the selected type of cell with a fluorescent compound and detecting the peak fluorescence of individual cells or a population of cells. The positional information for each cell or a population of cells is detected over a period of time by tracking the fluorescence and storing the data as pixel images of coordinates.

Albrecht-Buehler proposed a method for studying cell motility based upon observations of "phagokinetic tracks." G. Albrecht-Buehler, *Cell* 12, 333-339 (1977); G. Albrecht-Buehler, *Cell* 11, 395-404 (1977). In a most general way, a phagokinetic track is generated when a cell passes over a layer of "markers", and ingests them, leaving behind a blank spot equal to the area the cell has traversed. In principle the method is very powerful, as it provides a rapid and automatic method for integrating cell motility while preserving the history of individual paths. Until now, the method has only been used in a limited way due to problems with the available markers. Markers such as submicron Au (gold) particles, India ink or latex particles have been used because they can be imaged optically using darkfield microscopy. However, these markers also impose many limitations so that the technique has not received widespread acceptance.

The Au particles used in the phagokinetic tracking assay must be large (0.15 microns) in order to be observable optically. Such large particles do not stick well to the substrate, and therefore have to be grown directly on the substrate in a process that yields highly inhomogeneous particle distributions. Since the particles are grown directly on the substrates, by pouring a hot (near boiling) aqueous solution onto the substrate, the range of usable substrates is limited. Further, due to the large size of the Au microcrystals, when a cell moves one diameter, it ingests a volume of Au corresponding to ~1% of the total cell volume, and there is a strong possibility that this perturbs the cell motility. This is particularly true for small cells, such as epithelial cells, which are of particular importance in studies of metastasis, and in neurons. The film homogeneity is poor, and the inter-particle distance is large, limiting the resolution. Finally, this method provides only one level of contrast, so that it is restricted to measurements in two dimensions. Also it cannot easily be coupled to information about chemical signals involved in cell motility.

Albrecht-Buehler's method of phagokinetic tracking has previously been proposed as an in vitro cancer diagnostic assay. See Zetter, U.S. Pat. No. 4,359,527. The assay involved providing a substrate coated with a layer of visible particles susceptible to ingestion by capillary endothelial cells. Those cells are then seeded onto and allowed to adhere to the substrate. After incubation of the cells with a test sample (usually a fluid such as urine from a patient suspected of having cancer), the visible particle-detected phagokinetic tracks left by the cells are compared to the tracks left by a control sample. If the test tracks are larger, that indicates a positive cancer diagnosis. The track area is measured by fixing the cells and the tracks, projecting the tracks onto a television screen, tracing the projection on a transparent surface and automatically computing the track area on the surface using a digital image analyzer.

"Quantum dots," referred to herein as "semiconductor nanocrystals," are protein-sized crystals of inorganic semiconductor nanocrystals, initially developed for opto-electronic applications. Upon excitation by an energy source, semiconductor nanocrystals emit a signal. They are robust and efficient light emitters, with a wide range of potential applications in cell labeling.

The ability to control the growth conditions, shape and size allows one to tailor and control the optical properties of semiconductor nanocrystals. The absorption onset and emissions maximum of semiconductor nanocrystals shift to higher energy with decreasing size. See Bawendi et al., *J. Am. Chem. Soc.* 115, 8706 (1993). Variations of the material, size and shape used for the semiconductor nanocrystal afford a spectral range of 400 nm to 2 μm in the peak emission, with typical emission widths of 20-30 nm [full width at half maximum (FWHM)] in the visible region of the spectrum and large extinction coefficients in the visible and ultraviolet range. Various sizes of semiconductor nanocrystals can be excited with a single excitation wavelength of light, resulting in the simultaneous detection of multiple emission colors. See Alivisatos et al., *Science* 281, 2013 (1998).

Because biological applications require water-soluble semiconductor nanocrystals, several methods have been developed to add a solubilizing layer. One strategy relies on covalently coupling a thiolated molecule having a free carboxyl group facing the solution to maintain water solubility. See Nie et al., *Science* 281, 2016 (1998). However, because the bond holding the thiol to the semiconductor nanocrystal is dynamic, this leads to low stability in water and slow dissolution of the semiconductor nanocrystals and the diffusion. When coated with a suitable solubilizing layer, such as silica, the semiconductor nanocrystals are stable under physiological buffer conditions. See Gerion et al., *J. Phys. Chem B* 105, 8861-8871 (2001), "Synthesis and Properties of Biocompatible Water-Soluble Silica-Coated CdSe/ZnS Semiconductor Quantum Dots" and Mitchell et al., *J. Am. Chem. Soc.*, 121 (35), 8122-8123, 1999. These semiconductor nanocrystals maintain their optical properties and are soluble in solutions over a wide range of pH.

The silanization method to provide solubility to semiconductor nanocrystals is fully described in Gerion et al, *J. Phys. Chem B* 105, 8861-8871 (2001) and illustrated in FIG. 1 of the same reference. The method relies upon the siloxane bond (—Si—O—Si—) in the following reaction, wherein each Si atom is actually bound to three methoxy groups per molecule and one residual group, but the reaction shown only describes the reaction of one of the methoxy groups.

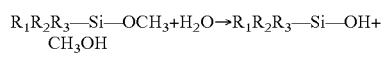

$R_1R_2R_3$—Si—OCH$_3$+H$_2$O→R$_1$R$_2$R$_3$—Si—OH+ CH$_3$OH

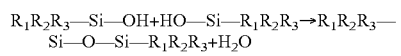

$R_1R_2R_3$—Si—OH+HO—Si—R$_1$R$_2$R$_3$→R$_1$R$_2$R$_3$— Si—O—Si—R$_1$R$_2$R$_3$+H$_2$O

Limitations on biological markers have prompted researchers to use semiconductor nanocrystals as fluorescent biological labels. See Bruchez et al., *Science* 281, 2013-2016 (1998). Others have developed "quantum dot" bioconjugates for detection by coupling luminescent semiconductor nanocrystals to biological molecules. For example, see Chan et al., *Science* 281, 2016-2018 (1998) and Bruchez et al., *Science* 281, 2013-2016 (1998). Hydroxylated "quantum dots" have recently been used as luminescent probes for in situ hybridization as demonstrated by Pathak et al., *J. Am. Chem. Soc.* 123, 4103-4104 (2001). "Quantum dots" have also been used to tag microbeads for multiplexed optical coding of biomolecules by embedding different-sized ZnS-capped CdSe semiconductor nanocrystals into polymeric microbeads. See Nie et al., *Nature Biotechnology* 19, 631-635 (2001).

Until now, "quantum dot" based biological labeling experiments have been confined to static labeling. Prior publications and usage of "quantum dots" in biological applications have been limited to these bioconjugate "quantum dots", where the semiconductor nanocrystals were decorated with proteins, antibodies, nucleic acids, oligonucleotides and other organo- or affinity molecules as hybridization probes in fluorescence assays or to mediate receptor-mediated endocytosis. Prior work using decorated semiconductor nanocrystals have all relied upon the attached biomolecules for entry into cells or for use in a specific biological application and have not attempted to use undecorated "quantum dots." See Alivisatos et al., U.S. Pat. No. 6,207,392.

BRIEF SUMMARY OF THE INVENTION

The present invention provides a method of using semiconductor nanocrystals for tracking cellular behavior and processes. The present invention is based on the inventors' finding that semiconductor nanocrystals are spontaneously taken up by a variety of cells, while remaining fully luminescent, thus enabling the tracking of dynamical cellular phenomena. Another aspect of the invention provides the ability to examine cellular behavior in live cells over extended time periods (from about 10 minutes to 10 days), and to quantify changes in response to various molecular manipulations. The invention has advantages of being simple, reliable, quantitative, and allowing for continuous monitoring and manipulation as conditions are varied.

Semiconductor nanocrystal-based cellular imaging as demonstrated here, promises to be a versatile and powerful method of quantifying motility in a wide variety of circumstances. Because the preparation of the markers has been separated from the process of substrate priming, a wide variety of culture surfaces can be used, including growth on extracellular matrix. This approach generates a thicker, but more natural, environment compared to glass cover slips. The semiconductor nanocrystals are robust and do not photobleach, and yet they are small enough to be non-perturbative to the cells, and to be useful for phagokinetic tracking of small epithelial cells that are responsible for 90% of cancers. Since the detection is luminescence based, the tracks can be observed using commonly available fluorescence microscopy methods, such as epi-fluorescence, scanning laser confocal and multi-photon microscopy or wide-field, deconvolution microscopy.

One aspect of the invention provides a method for assaying cell motility and migration, comprising a substrate having a culture surface coated with a layer of semiconductor nanocrystals. Motile and migratory cells deposited on this culture surface migrate over the culture surface and take up semiconductor nanocrystals, leaving depleted regions. Because the semiconductor nanocrystals fluoresce, regions of the culture surface can be imaged and quantified by analyzing the levels of fluorescence. Depleted regions indicate cell migratory pathways and regions of increased fluorescence indicate cells containing semiconductor nanocrystals. Even non-directional motility can be detected; those cells that are highly motile but demonstrate no directional displacement over time take up nanocrystals and leave clear zones around them rather than migratory paths.

The invention comprises a general method for determining metabolic properties of living cells, comprising: (1) providing a culture surface for supporting biological activity of said cells; (2) depositing a layer of semiconductor nanocrystals on said culture surface; (3) seeding a layer of said cells to the culture surface; (4) detecting the changes in said layer of semiconductor nanocrystals after at least sufficient time has elapsed to allow the seeded cells to take up said semiconductor nanocrystals as illustrated in FIGS. 2 and 3. The time may be between 10 minutes and 10 days, preferably for 30 minutes, and more preferably in the period of 3 hours to 24 hours. The method is further comprised of the step of detecting changes in said layer of semiconductor nanocrystals caused by movement of the cells. The method can be further comprised of the step of adding a marker to be taken up by the cells in addition to the layer of semiconductor nanocrystals, wherein said marker is selected from the group consisting of: semiconductor nanocrystals with a detectable property that is different from that of the semiconductor nanocrystals recited in step (2), and an organic fluorescent dye.

A second aspect of the invention comprises a method for phagokinetic tracking, comprising the steps of: providing a substrate having a culture surface coated with one or more patterned layers of semiconductor nanocrystals, comprised of patterned arrangements of semiconductor nanocrystals. Patterns can be used to deposit one or more different types of semiconductor nanocrystals. Depleted regions indicate cell migratory pathways and regions of increased fluorescence indicate cells containing semiconductor nanocrystals. Alternatively, cells can be imaged to observe the various types of semiconductor nanocrystals that have been taken up to provide information as to the migratory pathway taken.

A third aspect of the invention is to provide a method for studying cell motility multi-dimensionally. This method would encompass providing a substrate having a culture surface, wherein one or more layers of semiconductor nanocrystals are deposited on the surface in a vertical gradient. Without limiting the scope of the invention, the layers of semiconductor nanocrystals can be comprised of multiple types of semiconductor nanocrystals layered or patterned according to, but not limited to, size, shape, charge, color, identity or number of attached molecules, or other differentiating property of semiconductor nanocrystals or combinations thereof.

A fourth aspect of the invention is to provide a method for studying cellular uptake. Taking advantage of the observation that semiconductor nanocrystals remain inside cells over prolonged periods of time, this method can be used to compare and observe cellular uptake.

A fifth aspect of the invention is to provide a method for tracking cell lineage by taking advantage of the observation that semiconductor nanocrystals that are taken up by cells are subsequently passed on to daughter cells during cell division. This method enables tracking of live cellular population and lineage response to any varied cellular condition.

Another aspect of the invention is a method by which semiconductor nanocrystals with many emission colors can be prepared and bio-conjugated to a range of targeting molecules, so that it is possible to monitor cell motility and migration while simultaneously tracking specific proteins tagged with complementary fluorescent molecules such as Green-Fluorescent Protein (GFP), Cyan-Fluorescent Protein (CFP), Yellow Fluorescent Protein (YFP), Discoma Red Fluorescent Protein (DsRed) or Blue Fluorescent Protein (BFP) available from CLONTCH Laboratories, Inc., Palo Alto, Calif.

A further aspect of the invention includes using negative, positive or neutral charged semiconductor nanocrystals. These nanocrystals can be made by adding a hydrophilic outer shell to conventionally used semiconductor nanocrystals comprised of a semiconductor core and a semiconductor shell as shown in FIG. 1. The outer shell can be comprised of stabilizing and/or functional groups including, but not limited to, phosphonate silane, mercaptosilane, chlorotrimethylsilane, polyethylene glycol-silane, ammoniumsilane, thiol (—SH), amino (—NH$_2$), carboxyl (—COOH), alcohol (—OH), and phosphate (—PO$_3$) groups and combinations thereof.

A further aspect of the invention is a method for assaying the metastatic potential of malignant cells obtained from patients through biopsies or fluid samples.

A further aspect of the invention is a kit comprising a culture dish containing an extracellular matrix and one or more layers of semiconductor nanocrystals.

looks fairly continuous. After 24 hours large clearings in the semiconductor nanocrystals layer are observed around the tumor cells (D, E), but not the non-tumor cells (J, K). Images were collected with a confocal microscope using fluorescence detectors to examine the semiconductor nanocrystals (B, E, H, K) and DIC (Differential Interference Contrast) to visualize the cells (C, F, I, L); the merged images (A, D, G, J) show the cells and the layer of semiconductor nanocrystals.

Figure 6:
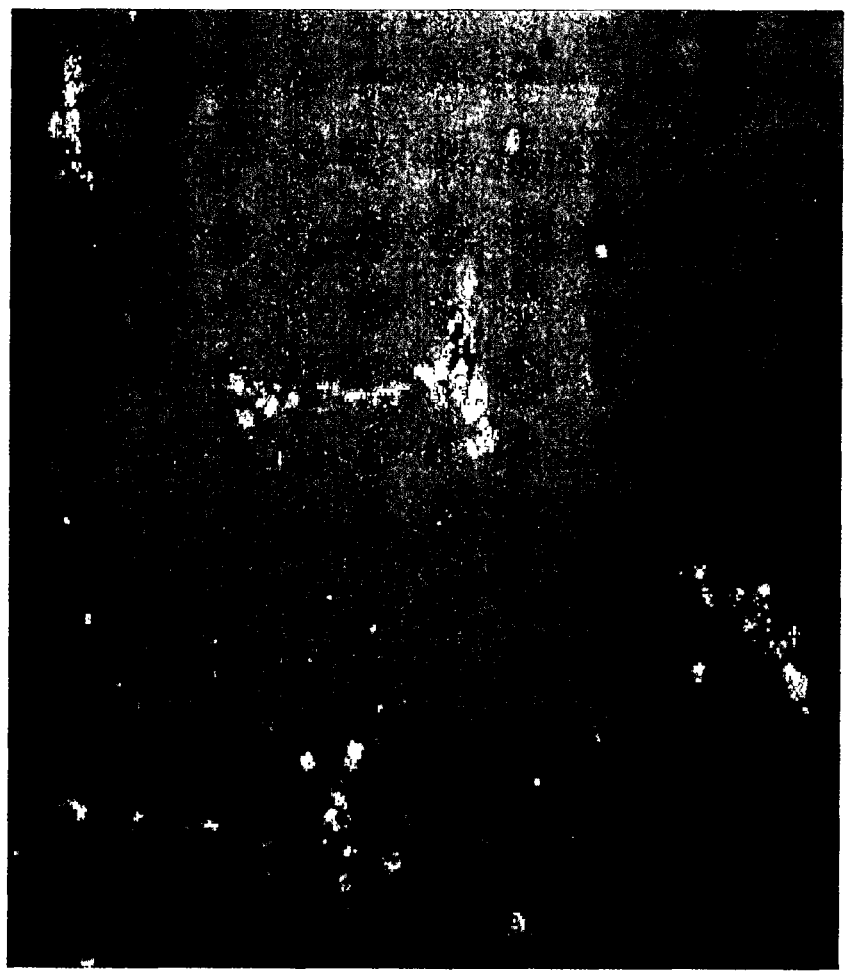

FIG. 6. The color photograph shows the mixed colonies formed by MCF 10A cells when co-cultured with MDA-MB-231 cells. The normal mammary epithelial MCF-10A cells are labeled in red, while the mammary epithelial tumorigenic MDA-MB-231 cells are labeled in green.

DETAILED DESCRIPTION OF THE PREFERRED EMBODIMENT

Definitions

The term "phagokinetic track" herein refers to a visible path generated when a cell passes over a layer of "markers", and takes up the "markers", leaving behind a region depleted of markers representing the area the cell has traversed. The term generally refers to a method to visualize a cell migratory pathway. It also refers to non-directional motility. Those cells that are highly motile but demonstrate no directional displacement over time take up markers and leave clear zones around them rather than migratory paths.

The term "markers" herein refers to semiconductor nanocrystals and structures including them, or other detectable particles, such as a dye.

The term "semiconductor nanocrystals" herein is used synonymously with the term "quantum dot" as commonly understood and herein refers to nanocrystals that are composed of a semiconducting material and are made in such a way as to crystallize in exceedingly small sizes, e.g. from 2-20 nm in diameter. The semiconductor nanocrystals used herein are colloidal, which refers to the fact that the semiconductor nanocrystals are dispersed within a continuous medium in a manner that prevents them from being filtered easily or settled rapidly. The semiconductor nanocrystals used herein luminesce upon excitation by a light source. The semiconductor nanocrystals used herein preferably are modified to be hydrophilic and may be further modified to contain functional groups, crosslinkers, biomolecules and combinations thereof.

The term "monolayer" herein refers to each atomic layer of the shell material grown around the core. Each monolayer increases the diameter of the shell material, and the optical properties of the semiconductor nanocrystals.

The term "substrate" herein refers to a material, for example, glass, plastic, petri dish, cover slip or filter membrane, onto which the culture surface can be applied or onto which the semiconductor nanocrystals and/or cells can be seeded.

The term "culture surface" herein refers to a surface suitable for deposition, maintaining metabolic activity of vertebrate cells and suitable for or incorporation of the semiconductor nanocrystals and suitable for seeding cells. This culture surface can be either the substrate itself or applied directly to the substrate. Exemplary culture surfaces are extracellular matrix (ECM) or components of the ECM, such as, preferably collagen, laminin and fibronectin.

The term "metastatic potential" herein refers to the probability or potential spread of a disease from the organ or tissue of origin to another part of the body. The term also herein generally refers to the transmission of pathogenic microorganisms or cancerous cells from an original site to one or more sites elsewhere in the body, usually by way of the blood vessels or lymphatics.

The term "motility" herein refers to cell behavior and movement. The term also refers to spontaneous and/or non-directional movement of cells—for examples, lamellipodial ruffling, crawling around the culture surface. Migration is a type of motility and cell migration and motility can be indicative of metastatic potential. The term "migration" herein refers to cell movement such as the crawling of cells from one tissue to another tissue, from tissue to blood stream to tissue, or (in the lab setting) from one side of a filter to the other. The term also describes directional migration and movement.

The term "chemotactic behavior" herein refers to cell migration towards a specific chemical stimulus.

The term "cell" herein refers to human, other vertebrate, insect, bacterial, plant, yeast, or other unicellular organisms.

The terms "cellular uptake" or "take[n] up" herein refer to the action of cells bringing foreign material, substances, or molecules inside the cell, without implying a specific mechanism of uptake. The terms are meant to include, but are not limited to, mechanisms such as specific or non-specific engulfment, pino-, endo-, and/or phagocytosis, or cellular ingestion.

The term "organic fluorescent dye" herein refers to a dye which is used to highlight cellular structures such as, but not limited to, nucleic acids, proteins, plasma membranes, endoplasmic reticulum, mitochondria and Golgi apparatus. Examples of appropriate dyes for use in this invention include, but are not limited to, actinomycin D, acridine orange, bisbenzimide, 4',6-Diamidino-2-phenylindole (DAPI), propidium iodide, ethidium bromide, carbocyanines, pyridinium dibromides, tetramethylrhodamine ethyl ester (TMRE), and ceramides. The term is also meant to include organic fluorescent dyes which are linked to biological molecules which recognize specific cellular structures. Examples of such are fluorescein-labeled phalloidin, which binds to and highlights the actin network, and specific proteins tagged with complementary fluorescent molecules (for example, GFP, CFP, YFP, or BFP) or other fluorescent dyes.

The term, "biological molecule" herein refers to molecules including, by way of example only, such classes of substances as monoclonal and polyclonal antibodies, nucleic acids (both monomeric and oligomeric), proteins, enzymes, lipids, polysaccharides, and small molecules such as sugars, peptides, drugs, and ligands.

Introduction

Figure 1:
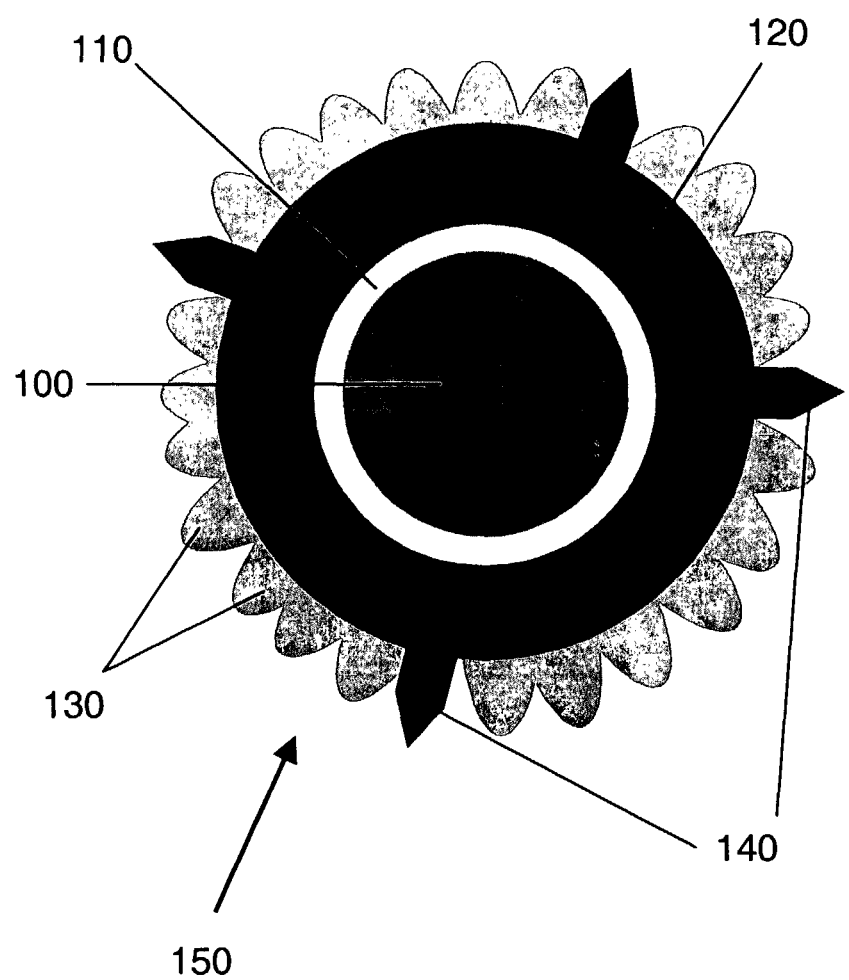
FIG. 1. Representation of a preferred semiconductor nanocrystal for use in the invention. The preferred semiconductor nanocrystal 150 is comprised of a semiconductor core 100, surrounded by a shell 110 of a second semiconductor material and an outer hydrophilic shell 120. The outer shell can be embedded with functional groups 130 and stabilizing groups 140.

According to the present invention, semiconductor nanocrystals as shown in FIG. 1 are spontaneously taken up by a wide variety of cells, while remaining fully luminescent, thus enabling the tracking of dynamical phenomena inside cells over periods of minutes to weeks, and demonstrating that this phenomenon can be used for semiconductor nanocrystal-based imaging of phagokinetic tracks.

The invention provides a general method for labeling vesicles of one or more selected cells contained in a sample, comprising the steps of: (1) providing a substrate having a culture surface, (2) depositing one or more layers of semiconductor nanocrystals onto said culture surface, (3) seeding said one or more selected cells onto said culture surface, (4) incubating said cells for an effective length of time to allow for said cells to take up one or more said semiconductor nanocrystals, (5) measuring the amount of semiconductor nanocrystals taken up by at least one of said one or more selected cells.

The uptake of semiconductor nanocrystals likely reflects non-specific engulfment via a process of pino-, endo-, and/or phagocytosis of the surrounding matrix. Semiconductor nanocrystals readily adhere to the cell surface, most likely due to interactions of the cell surface glycoproteins and glycolipids with the semiconductor nanocrystal surface. Addition of semiconductor nanocrystals to a dish of cells not previously exposed to semiconductor nanocrystals results in the almost immediate coating of the entire cell surface with semiconductor nanocrystals, clearly delineating all lamellipodia and filopodia. The same attraction probably occurs as cells encounter the semiconductor nanocrystals as they crawl across the matrix, resulting in adherence of semiconductor nanocrystals to the cell surface and subsequent uptake. It is less likely that the semiconductor nanocrystals trigger uptake via the process of receptor-mediated endocytosis, since they are non-biological, but it is possible that the associated matrix to which they are attached could trigger that process. Whatever the mechanism, cells take up semiconductor nanocrystals as they crawl, leaving behind a history of migratory movements and accumulating the evidence of their consumption in large perinuclear storage vesicles.

Using semiconductor nanocrystal-based phagokinetic tracking as demonstrated here, promises to be a versatile and powerful method of quantifying motility and migration in a wide variety of circumstances. Because the preparation of the markers has been separated from the process of substrate priming, a wide variety of tissue culture substrates can be used, including growth on extracellular matrix substances. This approach generates a thicker, but more natural, environment compared to glass cover slips. The semiconductor nanocrystals are robust and do not photobleach. Yet they are small enough to be non-perturbative to the cells, and to be useful for phagokinetic tracking of small cells.

Small epithelial cells tend to be responsible for 90% of all cancers. Epithelial cells, however, do not typically make phagokinetic tracks because they normally do not migrate. Therefore a phagokinetic track of epithelial cell migration suggests metastatic potential. A more detailed analysis or clinical diagnosis of cancerous cells that have metastasized would depend from the observation and analysis of a phagokinetic track. Comparison to the phagokinetic track, or lack of one, of a normal cell also indicates the potential or degree of potential metastasis of the cells being used in this method.

The size of the semiconductor nanocrystals have no effect on uptake, transport or storage of semiconductor nanocrystals. Since the detection is luminescence based, the tracks can be observed using fluorescence microscopy methods such as confocal and multi-photon microscopy.

Semiconductor nanocrystals with many emission colors can be prepared so that it is possible to monitor cell motility and migration while simultaneously tracking specific proteins tagged with complementary fluorescent molecules (for example, GFP, CFP, YFP, or BFP) or other fluorescent dyes. Additionally, a second dye may be used to label cell features in order to improve the visibility of the semiconductor nanocrystals that have been taken up by cells.

Figure 5:
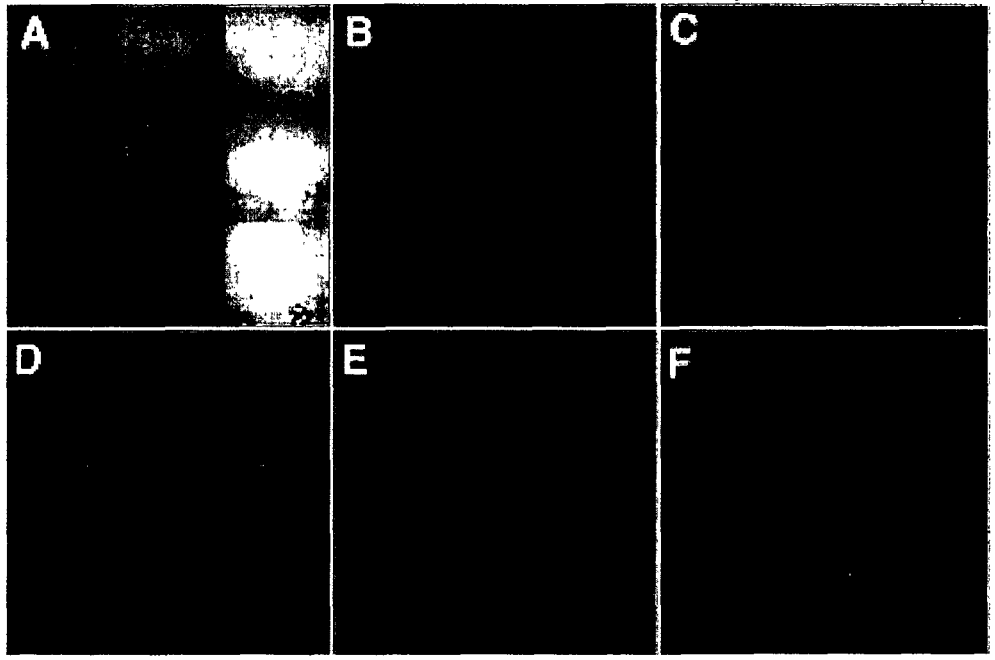
FIG. 5. Color photographs showing the uptake of semiconductor nanocrystals reveals phagokinetic tracks 190 of breast tumor cells. After 3 hours, the layer of semiconductor nanocrystals beneath the tumor cells (B) and non-tumor cells (H)
Figure 5:
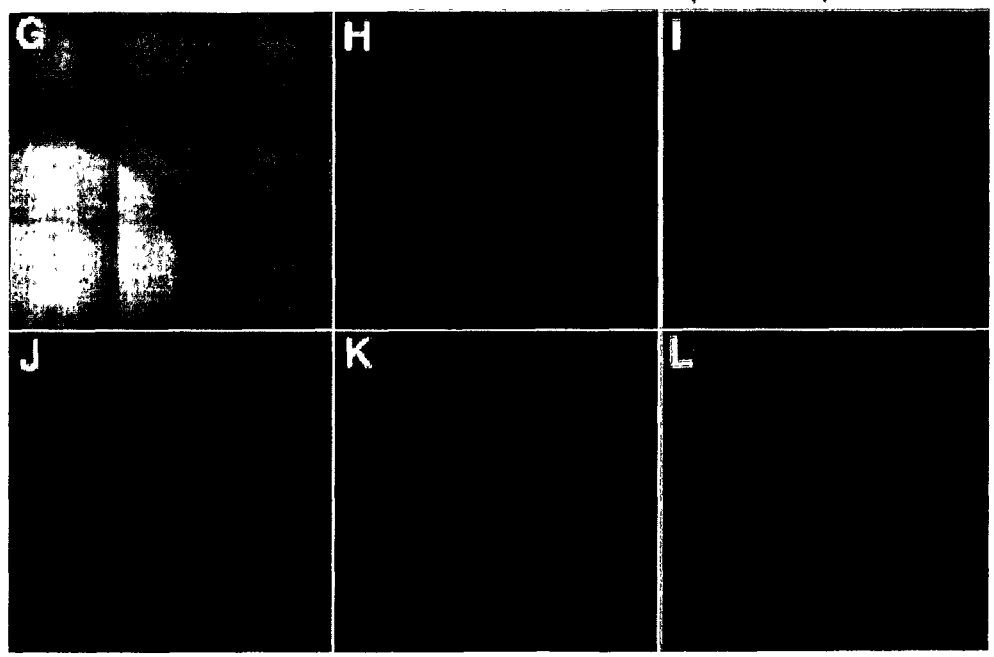

The degree of semiconductor nanocrystal uptake reflects the migratory behavior of the cells. Highly dedifferentiated, invasive mammary epithelial cancer cells, for example, voraciously take up semiconductor nanocrystals as they migrate. In doing so, they generate a region free of semiconductor nanocrystals that clearly reveals their migratory pathways, as can be seen in cells that were cultured on semiconductor nanocrystal-covered collagen for 24 hours (FIGS. 5D-F).

Other kinds of motility studies can be done, other than for diagnosis or indication of cancer. Other types of studies can use the method with motile cell types, including but not limited to, studies of sperm motility, macrophage invasion, bacteria and other prokaryotic cells, simple eukaryotic organisms such as yeast, *Dictyostelium discoideum* or *Caenorhabditis elegans*, and isolated cultured cells of vertebrates.

As long as one week after growth on semiconductor nanocrystal-coated collagen, all cells contained perinuclear semiconductor nanocrystals. Semiconductor nanocrystals are excluded from the nucleus. There is also no evidence of degradation of these semiconductor nanocrystals over time. Cells that were trypsanized, replated on collagen in the absence of semiconductor nanocrystals, and examined ten days later all contained large semiconductor nanocrystal-filled vesicles around the nucleus. Since there were no semiconductor nanocrystals on the extracellular matrix for new cells to take up, the semiconductor nanocrystals must have been passed to daughter cells during cell division.

Taking advantage of the fact that semiconductor nanocrystals are passed to daughter cells during cell division, provides a method for identifying cells of a specific lineage, comprising the steps of: (1) providing a substrate, having a culture surface, (2) depositing one or more layers of semiconductor nanocrystals onto said culture surface, (3) seeding cells onto said culture surface, (4) incubating said cells for an effective length of time to yield labeled cells that have taken up one or more said semiconductor nanocrystals, (5) allowing said cells to divide continuously and pass on said semiconductor nanocrystals that have been taken up to all daughter cells to create a population of labeled cells having semiconductor nanocrystals, and (6) using said population for biological applications.

These now labeled cells of different origins or types having taken up semiconductor nanocrystals can be used for further biological applications and study. For example, upon mixing the now labeled cells and seeding onto a culture surface, studies of live cell-cell interaction can be observed and tracked because the cells of the different lineages are clearly labeled and identifiable.

The semiconductor nanocrystals can also be used for lineage analyses in developing embryos. Injection of semiconductor nanocrystals into one embryonic cell early in development will enable the easy determination the progeny of that cell by looking for cells containing those semiconductor nanocrystals.

Finally, it is of great interest to study migration and motility in three dimensions in layered extracellular matrix media. In one embodiment, semiconductor nanocrystals of different properties are deposited in a vertical gradient in a culture substrate, providing depth contrast. Semiconductor nanocrystal-based phagokinetic tracking can thus lead to a wide range of new methods for the quantification of cell migration and the rapid assessment of metastatic potential.

A. The Semiconductor Nanocrystals 150

Referring now to FIG. 1, a preferred semiconductor nanocrystal 150 having a core/shell configuration is shown. The preferred semiconductor nanocrystals described herein require at least two layers. First, a first semiconductor material (e.g. CdSe) forms a core 100. The core provides the semiconductor nanocrystal structure and is essential for luminescence. Second, the preferred semiconductor nanocrystals comprise an essential outer layer that provides hydrophilicity and is described herein at section 2.

(1) Semiconductor Nanocrystal Core 100 and Shell 110

The semiconductor materials useful in forming the semiconductor nanocrystal core 100 include Group II-VI semiconductors such as MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe as well as mixed compositions thereof; as well as Group III-V semiconductors such as GaAs, InGaAs, InP, and InAs and mixed compositions thereof. As mentioned above, the use of Group IV semiconductors such as germanium or silicon, or the use of organic semiconductors, may also be feasible under certain conditions. The semiconductor nanocrystals may also include alloys comprising two or more semiconductors selected from the group consisting of the above Group III-V compounds, Group II-VI compounds, Group IV elements, and combinations thereof.

Formation of such core/shell semiconductor nanocrystals is described more fully in Example 1 and in a publication entitled "Epitaxial Growth of Highly Luminescent CdSe/CdS Core/Shell Nanocrystals with Photostability and Electronic Accessibility", by Peng, Schlamp, Kadavanich, and Alivisatos, published in the *Journal of the American Chemical Society*, Volume 119, No. 30. 1997, at pages 7019-7029, the subject matter of which is hereby specifically incorporated herein by reference.

The formation of the semiconductor nanocrystals employed in the present invention are preferably made according to the method of formation of semiconductor nanocrystals of Group III-V semiconductors as described in commonly assigned Alivisatos et al. U.S. Pat. Nos. 5,751,018; 5,505,928; and 5,262,357, which also describe the formation of Group II-VI semiconductor nanocrystals. Also described therein is the control of the size of the semiconductor nanocrystals during formation using crystal growth terminators. The teachings of Alivisatos et al. in U.S. Pat. Nos. 5,751,018; 5,262,357; 5,505,928; and 5,262,357 are each hereby specifically incorporated by reference in their entirety. The teachings of the aforementioned U.S. patents represent illustrative but not exhaustive examples of suitable semiconductor nanocrystals as contemplated for use in this invention.

A shell 110 of another semiconductor material (e.g. ZnS or CdS) can be grown over the core semiconductor material between the core and the outer hydrophilic layer to a thickness of, for example, 1-10 monolayers in thickness. This optional shell or shells between the soluble shell 120 and the core 100 of the semiconductor material is added to enhance the optical properties of the nanocrystals, but is not essential to facilitate uptake by cells. When, for example, a 1-10 monolayer thick shell of CdS or ZnS is epitaxially grown over a core of CdSe, there is a dramatic increase in the room temperature photoluminescence quantum yield.

(2) Semiconductor Nanocrystal Outer Hydrophilic Shell 120

The semiconductor nanocrystals useful in this invention should be soluble. In order to confer water solubility, the hydrophobic (core or core/shell) semiconductor nanocrystals are coated with an outer hydrophilic shell 120. This layer can be, for example a siloxane shell, but also could be composed of other materials, for example, but not limited to, mercapto hydrocarbonic acids.

References for making said silica shell include Alivisatos et al., Semiconductor Nanocrystals as Fluorescent Biological Labels. *Science*, 281, 2013-2016 Sep. 25, 1998; Gerion, D. et al., Synthesis and Properties of Biocompatible Water-Soluble Silica-Coated CdSe/ZnS Semiconductor Quantum Dots. *Journal of Physical Chemistry B*, 105(37), 8861-8871 (2001) and Parak, W. J. et al. Conjugation of DNA to silanized colloidal semiconductor nanocrystaline quantum dots, *Chem. Mat.* 14, 2113-2119 (2002), all of which are hereby incorporated by reference in their entirety.

Similar to the various compositions of semiconductor nanocrystals that are useful in practicing this invention, the invention can be practiced with various types of semiconductor nanocrystals. These types include but are in no way limited to various color, size, shape, charge, identity or number of attached molecules, chemical or organic surface, or other differentiating property of semiconductor nanocrystals or combinations thereof. The practice of this invention is greatly enhanced by using more than one differentiating semiconductor nanocrystal property that can be detected. This significantly increases the number of differentiating properties that can be exploited and enables one to practice the invention and observe one or more phenomena in parallel.

(3) Stabilizing Groups 130

In order to further make the semiconductor nanocrystals soluble, special stabilizing groups 130 can be introduced on the surface of the semiconductor nanocrystals: either charged groups or groups that facilitate steric repulsion. Positively charged, neutral or negatively charged semiconductor nanocrystals may enter cells differently. Stabilizing groups are attached to the outer shell of the semiconductor nanocrystals. Examples of such stabilizing groups that stabilize semiconductor nanocrystals in water may include, but are not limited to, -phosphonate (negatively charged), -carboxyl (negatively charged), polyethylene glycol (PEG which is neutral and provides steric repulsion), and -ammonium (positively charged).

Methods of making negatively charged semiconductor nanocrystals are described by D. Gerion et al., *Journal of Physical Chemistry B*, 105(37), 8861-8871, (2001). A method of making positively charged and almost neutral semiconductor nanocrystals is described in Example 1 and by W. J. Parak et al., *Chemistry of Materials*, 2002; 14(5); 2113-2119.

Other strategies for generating water-soluble semiconductor nanocrystals have been developed by other groups as demonstrated in Mattoussi, H. et al., Bioconjugation of Highly Luminescent Colloidal CdSe—ZnS Quantum Dots with an Engineered Two-Domain Recombinant Protein. *Physica Status Solidi B*, 224(1), 277-283, 2001; Chan, W. C. W. and Nie, S., 1998. Quantum Dot Bioconjugates for Ultrasensitive Nonisotopic Detection. *Science*, 281(SEPTEMBER 25), 2016-2018, and are hereby incorporated by reference in their entirety.

Different organic molecules linked on the semiconductor nanocrystal may also influence cellular uptake. Such molecules can be linked to the surface of the semiconductor nanocrystal as described by the teachings of Alivisatos et al., U.S. Pat. Nos. 5,990,479 and 6,207,392, which are hereby incorporated by reference in their entirety.

(4) Functional Groups 140 Attached to Semiconductor Nanocrystals

In addition to stabilizing groups added to the outer shell, functional groups can be added. These functional groups act as linking groups and permit the attachment of other types of molecules to the semiconductor nanocrystal surface. Examples of such functional groups include, but are not limited to, thiol (—SH), amino (—$NH_2$), carboxyl (—COOH), alcohol (—OH), and phosphate (—$PO_3$) groups.

Semiconductor nanocrystals having biological molecules attached to the functional group of the semiconductor nanocrystal is known in the art and can be employed in this invention as well. Semiconductor nanocrystals having biological molecules attached are preferably made according to the methods and process for making and using such nanocrystals as taught by Alivisatos et al. U.S. Pat. No. 6,207,392, the teachings of which are hereby incorporated by reference in their entirety.

Basically any biological molecule can be attached to these functional groups. The attachment can be covalent. Use of bifunctional crosslinker molecules can accomplish this purpose. Examples of biological molecules which can then be attached to these functional groups are discussed in the next section. As shown in FIG. 1, the semiconductor nanocrystal has a core, surrounded by a shell, and an outer hydrophilic shell. Stabilizing groups are embedded on the outer shell for water solubility. Embedding functional groups in the outer shell is optional but helpful should the user desire to link other molecules to the semiconductor nanocrystal.

Basically, biological molecules may comprise any molecule capable of being linked to one or more semiconductor nanocrystal compounds which is also capable of specific recognition of a particular detectable substance. In general, any affinity molecule useful in the prior art in combination with a dye molecule to provide specific recognition of a detectable substance will find utility in the formation of the semiconductor nanocrystals of the invention. Such molecules include, by way of example only, such classes of substances as monoclonal and polyclonal antibodies, nucleic acids (both monomeric and oligomeric), proteins, enzymes, lipids, polysaccharides, and small molecules such as sugars, peptides, drugs, and ligands. Lists of such molecules are available in the published literature such as, by way of example, the "Handbook of Fluorescent Probes and Research Chemicals", (sixth edition) by R. P. Haugland, available from Molecular Probes, Inc.

Attaching biological molecules onto different types of semiconductor nanocrystals allows the investigation of cells in parallel by providing a way to easily differentiate between test biological molecules. For example, attachment of molecule A to a red semiconductor nanocrystal can be differentiated easily from a green semiconductor nanocrystal having attached molecule B. Alternatively, studying how different biological molecules change the spontaneous and indiscriminate uptake of semiconductor nanocrystals is another application of this invention.

Additional embodiments of the invention can be envisioned when semiconductor nanocrystals with many emission colors are prepared and bio-conjugated to a range of targeting molecules, so that it is possible to monitor cell motility and migration while simultaneously tracking specific proteins tagged with complementary fluorescent molecules (e.g. GFP, CFP, YFP, or BFP).

(5) Color Emitted by Semiconductor Nanocrystals

The semiconductor nanocrystals used in the preferred embodiment will have a capability of absorbing radiation over a broad wavelength band. This wavelength band includes the range from gamma radiation to microwave radiation. In addition, these semiconductor nanocrystals will have a capability of emitting radiation within a narrow wavelength band of about 40 nm or less, preferably about 20 nm or less, thus permitting the simultaneous use of a plurality of differently colored semiconductor nanocrystals with different semiconductor nanocrystals without overlap (or with a small amount of overlap) in wavelengths of emitted light when exposed to the same energy source.

Both the absorption and emission properties of semiconductor nanocrystals may serve as advantages over dye molecules which have narrow wavelength bands of absorption (e.g. about 30-50 nm) and broad wavelength bands of emission (e.g. about 100 nm) and broad tails of emission (e.g. another 100 nm) on the red side of the spectrum. Both of these properties of dyes impair the ability to use a plurality of differently colored dyes when exposed to the same energy source.

Multiplexing is enabled by this embodiment because of the broad bandwidth at which the semiconductor nanocrystals are excitable. One may use a common excitation source for the simultaneous excitation of several semiconductor nanocrystals, i.e., several semiconductor nanocrystals which give off radiation at different frequencies, thus permitting simultaneous excitation and detection of the presence of several semiconductor nanocrystals indicating, for example, the presence of several detectable substances in the material being examined.

The number of colors of semiconductor nanocrystals that can be resolved in parallel can be calculated on the rule of Full Width Half Maximum (FWHM). For example, based on the rule of FWHM and a wavelength range of approximately 400 to 800 nanometers, approximately 20 different colors of semiconductor nanocrystals could be resolved in parallel.

The frequency or wavelength of the narrow wavelength band of light emitted from the semiconductor nanocrystal may be selected according to the physical properties, such as size, of the semiconductor nanocrystal. The wavelength band of light emitted by the semiconductor nanocrystal, formed using the above embodiment, may be determined by either (1) the size of the core, or (2) the size of the core and the size of the shell, depending on the composition of the core and shell of the semiconductor nanocrystal. For example, a semiconductor nanocrystal composed of a 3 nm core of CdSe and a 2 nm thick shell of CdS will emit a narrow wavelength band of light with a peak intensity wavelength of 600 nm. In contrast, a semiconductor nanocrystal composed of a 3 nm core of CdSe and a 2 nm thick shell of ZnS will emit a narrow wavelength band of light with a peak intensity wavelength of 560 nm.

A plurality of alternatives to changing the size of the semiconductor nanocrystals in order to selectably manipulate the emission wavelength of semiconductor nanocrystals exist. These alternatives include: (1) varying the composition of the semiconductor nanocrystal, and (2) adding a plurality of shells around the core of the semiconductor nanocrystal in the form of concentric shells. It should be noted that different wavelengths can also be obtained in multiple shell type semiconductor nanocrystals by respectively using different semiconductor materials in different shells, i.e., by not using the same semiconductor material in each of the plurality of concentric shells.

(6) Size of Semiconductor Nanocrystals

Cells, which typically can range in size from 10-100 μm, can take up bacteria that are 1-2 microns long. The semiconductor nanocrystals useful in this invention preferably range in size from 2 nanometers (nm) to 2 microns in diameter; more preferably range in size from 2 nm to 1 micron in diameter; and even more preferably from 2 nm to 100 nm in diameter.

In a preferred embodiment, CdSe(2.8 nm)/ZnS/SiO$_2$ semiconductor nanocrystals, 8 nm total diameter and CdSe(4.1 nm)/ZnS/SiO$_2$ semiconductor nanocrystals, 16 nm outer diameter, are used, as described by D. Gerion et al., Synthesis and Properties of Biocompatible Water-Soluble Silica-Coated CdSe/ZnS Semiconductor Quantum Dots, 105(37), 886-8871 *Journal of Physical Chemistry B* (2001) and Parak, W. J. et al. Conjugation of DNA to silanized colloidal semiconductor nanocrystaline quantum dots. *Chem. Mat.* 14, 2113-2119 (2002).

A plurality of alternatives to changing the size of the semiconductor nanocrystals which also manipulate the emission wavelength of semiconductor nanocrystals exist. These alternatives include: (1) varying the composition of the semiconductor nanocrystal, and (2) adding a plurality of shells around the core of the semiconductor nanocrystal in the form of concentric shells.

(7) Shape of Semiconductor Nanocrystals

To date, semiconductor nanocrystals have all been approximately spherical in shape. The Figures demonstrate the invention using these approximately spherical semiconductor nanocrystals, but in no way limit the invention in terms of the shape of the semiconductor nanocrystals. Semiconductor nanocrystals of different shapes are suitable for use is within the contemplation of this invention. Alivisatos et al. have published methods of synthesizing various shaped semiconductor nanocyrstals, in *J. Am. Chem. Soc.* 122, 12700-12706 (2000), such as rods, arrows, teardrops and tetrapods, and is hereby incorporated by reference in its entirety.

(8) Other properties of Semiconductor Nanocrystals

Recently rod-shaped semiconductor nanocrystals were synthesized by the inventor and reported in Alivisatos et al., "Shape control of CdSe nanocrystals," *Nature* 404, 59 (2000), which is herein incorporated by reference in its entirety. When embedded in a polymer and stretched in one dimension, these rod-shaped semiconductor nanocrystals were found to preferentially polarize light parallel to that direction, thus demonstrating another distinguishing physical property of semiconductor nanocrystals that can be used in this invention. Other differentiating properties of semiconductor nanocrystals include but are in no way limited to water solubility, pH, toxicity, etc.

B. The Semiconductor Nanocrystal Apparatus

Figure 2:
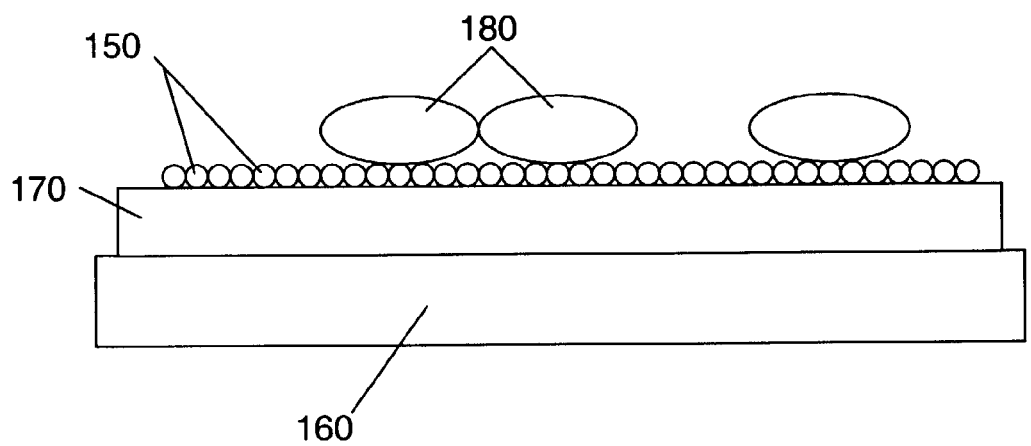
FIG. 2. Representation of a preferred semiconductor nanocrystal apparatus. The embodiment is shown before cells have taken up semiconductor nanocrystals. The substrate 160, having a culture surface 170, with a layer of semiconductor nanocrystals 150 deposited onto the substrate is seeded with cells 180 as shown.

Referring now to FIG. 2, the semiconductor nanocrystal apparatus is herein described. The apparatus is comprised of a substrate 160, having a culture surface 170, with a layer of semiconductor nanocrystals 150 deposited onto the substrate is seeded with cells 180 as shown. After cells have taken up semiconductor nanocrystals, the semiconductor nanocrystal-depleted areas or phagokinetic track 190 indicate where a cell has migrated. A light source 200 excites the semiconductor nanocrystals with light 220 and images are collected and recorded by an imaging system 210.

(1) Substrate 160

In a preferred embodiment, the substrate will be suitable for viewing under a microscope. Suitable substrates include materials such as, but not limited to, glass, petri dishes, culture dishes and chambers, gold or other metal coated glass, etc. The geometry of the substrate may be varied as well to include, but not limited to, planar surfaces, microstructured surfaces with furrows, grooves or other microstructures, and non-planar surfaces. Semiconductor nanocrystals would be perfect for use in microstructured substrates because of their small size and variability.

Patterning and guiding cell growth and observing cell migration along these microstructures has begun to be of some study and interest as shown by example, in Fromherz et al., "Electrical synapses by guided growth of cultured neurons from the snail Lymnaea stagnalis," *Biol Cybern* 82(4): L1-L5 (April 2000); and Whitesides et al., Selective Deposition of Proteins and Cells in Arrays of Microwells, *Langmuir* 17, 2828-2834 (2001).

Useful applications of this invention include, but are not limited to the following. Semiconductor nanocrystals could also be deposited into grooves of the microstructures. Or alternatively, the entire microstructure surface can be coated with a homogenous layer of semiconductor nanocrystals. This provides a way of observing whether cells, for example, preferentially follow the grooves in microstructures or not. The outgrowth or migration of the cells along the microstructure can be easily visualized and tracked as the semiconductor nanocrystals are incorporated into the cells.

(2) Culture surface 170

The culture surface in a preferred embodiment is comprised of extracellular matrix (ECM), which itself is comprised of one or more ECM proteins such as, but not limited to, collagen, laminin, fibronectin, elastin, nidogen/enactin and proteoglycan. The culture surface may also be comprised of other components, including growth and attachment factors. Those skilled in the art have typically been using one ECM protein in their assays but are moving towards the use of ECM that more resembles the ECM or basement membrane. An example of a suitable culture surface is BD MATRIGEL™ Matrix (Becton Dickinson Labware, Bedford, Mass.), which is a commercially available ECM that contains reconstituted basement membrane proteins, and other growth and attachment factors. In some embodiments wherein tumorigenic cells are used, it is preferred that the ECM used be growth factor reduced because the addition of growth factor in the culture surface may affect cell growth and morphology.

A preferred culture surface can also be used for a three-dimensional (3D) gel. A 3D gel allows the cells to be seeded on or within the culture surface and thus, cells can be observed growing on the culture surface or burrowing into or within the culture surface. Such culture surfaces provide a unique look at cell morphology and would prove useful in this invention to study cell motility.

In another preferred embodiment, the culture surface is comprised of a matrix that is capable of being in a liquid and a solid phase, such as, but not limited to growth agar, agarose, and other types of growth media.

The culture surface is applied directly to the substrate of choice and may be subsequently dried if necessary. Alternatively, the culture surface could be the substrate itself (e.g. glass, plastic) should the practice of the invention require it.

(3) Cells 180

Possible types of cells that may be used in the preferred embodiment of the invention include, but are in no way limited to, epithelial cells, fibroblasts, and macrophages.

Epithelial cells are involved in about 90% of cancers and are therefore particularly appropriate for use in this invention. Types of epithelial cells that can be used include, but are not limited to, mammary, lung, liver, kidney, prostate, pancreas, ovary, testes, uterus, intestine (colon, small intestine, large intestine) stomach, esophagus, skin, mouth (larynx, pharynx) as well as other cell lines from other tissues. Epithelial cell types that have been tested and are appropriate for use in this invention included human mammary epithelial cell lines that are immortalized or tumorigenic.

The invention should not be limited as to origin of the cells that can be used to practice the invention. Therefore, all tumor cell lines that are available from the American Type Culture Collection would be deemed appropriate cells used in the invention. See ATCC brochure, CB07-0300-05-1, at www.atcc.org/pdf/tcl.pdf. which is a listing of over 700 human cancer cell lines. Cancer cell lines from other organisms have also been contemplated as appropriate for use in the invention.

Other candidate cells appropriate for use in this invention include migratory cells such as fibroblasts, and macrophages, which exhibit chemotactic behavior.

In another aspect of the invention, cells taken from a patient biopsy are seeded onto the culture surface that is coated with semiconductor nanocrystals, and observed for metstatic potential as evidenced by the cells' metabolic properties, namely the property of motility which results in a phagokinetic track.

In yet another aspect of the invention, microorganisms may be used. The invention should prove useful for labeling microorganisms and studying motility in microorganisms. Suitable microorganisms (e.g. bacteria, yeast, algae) are cultured on a culture substrate designed to support growth of the selected microorganism (e.g. agar).

Another aspect of the invention contemplates multiple cell types or cells of varying origin seeded onto a culture surface, thus permitting the observation of interaction between these different cell types. In this embodiment of the invention, the first type of cells would have been seeded onto a culture surface and allowed to take up a sufficient amount of semiconductor nanocrystals for a period of time to pass on to daughter cells. A sufficient period of time is around 20-50 minutes to allow a sufficient number of semiconductor nanocrystals to be taken up by the parent cells. However, depending on the length of imaging time, this incubation period to allow cellular uptake of semiconductor nanocrystals can be shortened or extended.

Cells of different origins or types would have been seeded onto separate culture surfaces and allowed to take up a sufficient amount of semiconductor nanocrystals having a different detectable properties to label each type of cell. Upon mixing both types of semiconductor nanocrystal labeled cells and seeding onto a culture surface, studies of live cell-cell interaction can be observed.

In all cases, growth media appropriate to the cell type, containing necessary proteins, vitamins and other additives, such as pituitary extract, growth factors, insulin, and hydrocortisone, may be added to the cells when needed to promote and maintain cell growth and function.

(4) Deposition Methods

Various methods of deposition of semiconductor nanocrystals onto a culture surface can be used with this invention. The method contemplates the deposition of semiconductor nanocrystals onto a layer of cells seeded onto the culture surface by micropipetting or like means to allow cells to take up the semiconductor nanocrystals.

These culture surfaces also enable the incorporation of semiconductor nanocrystals into the matrix. For example, a first liquid layer of matrix is poured into a dish. Before the matrix hardens into solid phase, a volume of selected semiconductor nanocrystals is added. Diffusion of the semiconductor nanocrystals would allow the selected type of semiconductor nanocrystal to be incorporated into the first layer. After the first layer has cooled and solidified, a second layer of matrix is poured on the first and a volume of a second selected type of semiconductor nanocrystal is allowed to diffuse through the second layer.

An alternative culture surface is made by the deposition of layers of semiconductor nanocrystals between layers of matrix. After each layer of matrix cools, a volume of semiconductor nanocrystals can be added and spun dry similar to the method commonly used to plate bacteria onto bacterial plates or other equivalent means. Additional variations include, but are not limited to combinations of these two methods of depositing on or embedding semiconductor nanocrystals in a culture surface. After cells are seeded on the culture surface and begin to migrate through the culture surface, the paths of individual cells or populations of cells may be tracked by observing the type of semiconductor nanocrystals taken up.

Alternatively, in another variation, the cells can be mixed with the culture surface and semiconductor nanocrystals rather than seeded onto the surface as in the case of a three-dimensional culture surface. After the culture surface solidifies, the tracks of individual cells or populations of cells may be tracked by observing the type of semiconductor nanocrystals taken up by the cells.

Other deposition methods include, but are not limited to adding a solution of semiconductor nanocrystals to a culture surface and spreading it homogenously on the substrate, or by micropipetting semiconductor nanocrystals into discrete linear or patterned arrangements on selected regions of the culture surface, rather than a homogenous coating of semiconductor nanocrystals on the surface. Patterned arrangements allow deposition of several different types of semiconductor nanocrystals onto the culture surface. Linear arrangements of semiconductor nanocrystals are set spatially apart when deposited onto the surface, preferably at minimum 0.5 microns—20 microns apart, which is the approximate width of an average cell. Cells can range in size, for example, from sperm (0.5×1.0 micron diameter head) to red blood cells (7.5 micron diameter) to neurons (5-10 micron diameter cell body and long, thin extensions) to white blood cells (15-20 micron diameter).

C. Detecting Cells and Semiconductor Nanocrystals

Figure 3:
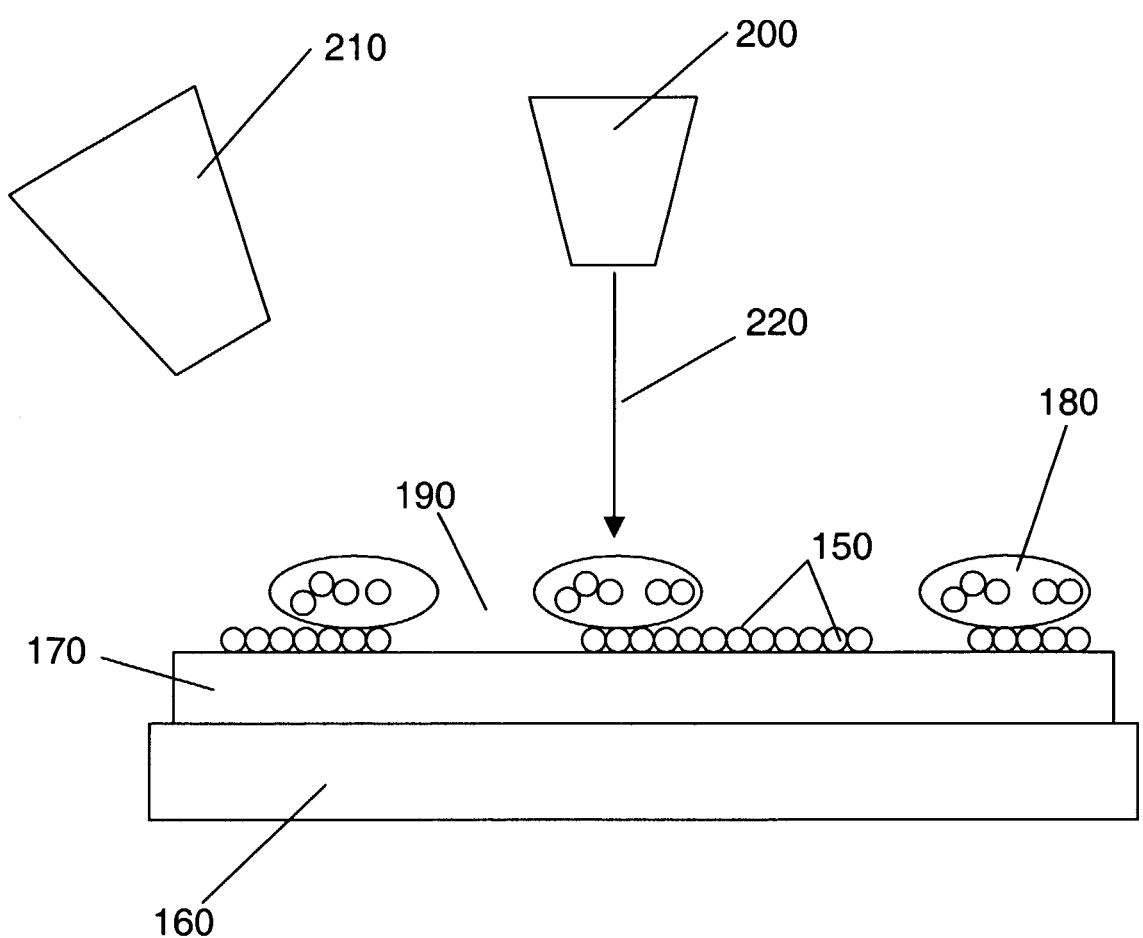
FIG. 3. Representation of a preferred embodiment after cells have taken up semiconductor nanocrystals and are being imaged. The semiconductor nanocrystal-depleted areas or phagokinetic track 190 indicate where a cell has migrated. A light source 200 excites the semiconductor nanocrystals with light 220 and images are collected and recorded by an imaging system 210.

A typical set up is shown in FIGS. 2 and 3. After the cells 180 are incubated for an effective length of time to allow for the cells to take up the semiconductor nanocrystals. The semiconductor nanocrystal-depleted areas 190 indicate where a cell has migrated. A light source 200 excites the semiconductor nanocrystals and images are collected and recorded by an imaging system 210.

(1) Light Sources and Imaging Systems

Optical excitation of the semiconductor nanocrystals is preferable, however, electromagnetic radiation of wavelength ranging from x-ray to ultraviolet to visible to infrared waves may be used to excite the semiconductor nanocrystals. In general, any light source 200 with an emission spectrum with a wavelength shorter than the wavelength of emission of the semiconductor nanocrystals can be used. Examples of effective light sources include, but are not limited to, a high-intensity light source such as a mercury lamp or xenon lamp, a laser, halogen lamp, light emitting diode (LED), or hand-held UV lamps. Although x-rays and electronic beams may be used, there may be problems using these in the present invention due to absorption of the beams by other elements of the invention such as petri dishes or water.

Referring to FIG. 3, the semiconductor nanocrystals are illuminated by a light source 200, preferably by a laser, and more preferably by a krypton-argon or Ti-Sapphire laser from an appropriate distance at an appropriate wavelength. Many light sources are possible and appropriate for use in the invention. For epi-fluorescence, one can use a mercury lamp or xenon lamp and record the image using a 35 mm camera, a digital camera, or a CCD camera. Many different lasers can be used, including argon, krypton-argon, helium-neon, and Ti-sapphire lasers typically used with confocal and multi-photon microscopy.

Detecting of cells that have taken up semiconductor nanocrystals can be carried out by various imaging systems 210 that include, but are not limited to, confocal fluorescence microscopy and multi-photon microscopy. Images, for example, can be collected with a confocal microscope using fluorescence detectors to examine the semiconductor nanocrystals and transmitted light, phase contrast, and DIC (Differential Interference Contrast) to visualize the cells. Two-photon excitation at appropriate wavelengths with a Ti-sapphire laser or one-photon excitation with a krypton-argon laser can be used to excite the semiconductor nanocrystals so that optical sections of the cells can obtained using confocal microscopy.

Figure 4:
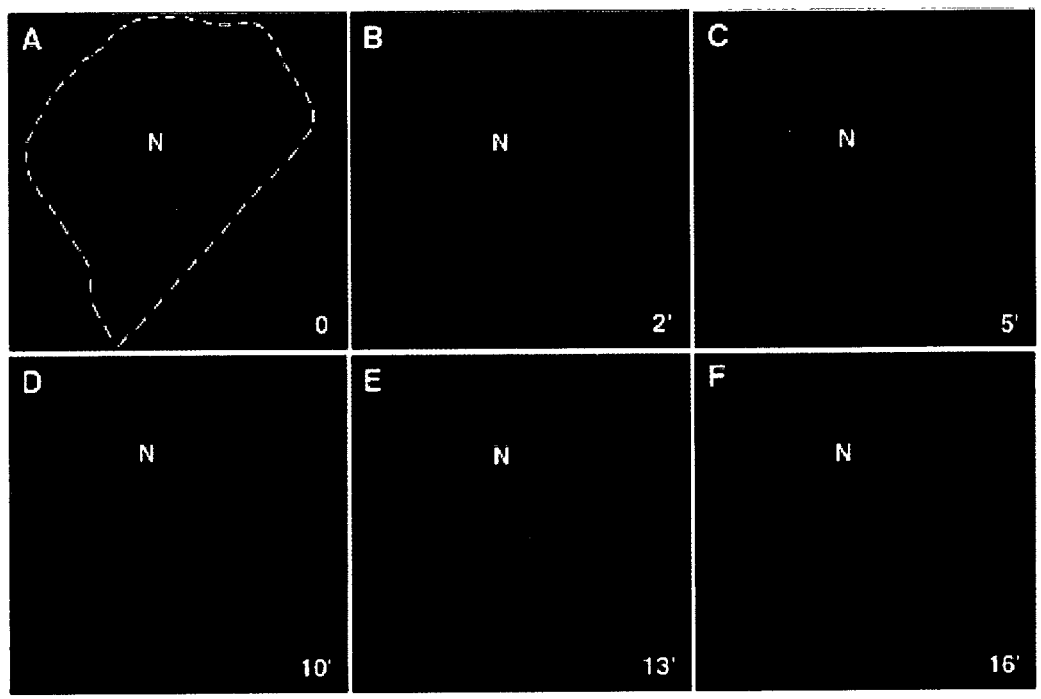
FIG. 4. Color photographs show uptake and transport of semiconductor nanocrystals by breast tumor cells as compared to standard organic fluorescent dyes. The organic fluorescent dye was rapidly internalized, and packaged in small vesicles (seen in red in FIGS. 4A-B). The cells also have taken up the semiconductor nanocrystals and incorporated them into small, but initially separate vesicles (green). The cells were examined over time by collecting images every 30 seconds using confocal microscopy. The designation "N" refers to the nucleus of the cell, which is unlabelled. The organic fluorescent dye suffered from marked photobleaching and was barely detectable after 5 min (FIG. 4C) and not detectable after 10 min (FIG. 4D). In contrast, the semiconductor nanocrystals demonstrated no photobleaching. Multiple semiconductor nanocrystal-filled vesicles are seen in the cytoplasm; one such vesicle (blue arrow) can be seen traveling from the cell periphery toward the nucleus.

For examples, in the color photographs of FIG. 4, cells were examined using the MRC-1024 laser scanning confocal microscope (Bio-Rad Laboratories, Hercules, Calif.) with a Nikon DIAPHOT 200 microscope and a 60× PLANAPO oil immersion objective lens (1.4 numerical aperture) (Nikon USA, Melville, N.Y.). Semiconductor nanocrystals were excited using a krypton-argon laser at 488 nm in this example. Z-series (successive images collected by stepping through the cell at 0.2-0.5 µm intervals) were obtained to determine distribution of the semiconductor nanocrystals and time-series (same optical section imaged at 30-second intervals over time) were obtained to examine the dynamics of semiconductor nanocrystals in the cells. For FIG. 5, cells were examined using a Zeiss 510 NLO imaging system (Carl Zeiss Micro-Imaging, Inc., Thornwood, N.Y.) while semiconductor nanocrystals were excited using an argon laser at 488 nm or Ti-Sapphire laser at 760 nm.

(2) Imaging Cells

Referring now to FIG. 4, regions of increased green fluorescence indicate cells containing semiconductor nanocrystals. Cells can be imaged to observe the various types and amounts of semiconductor nanocrystals that have been taken up by cells to provide information as to the migratory pathway taken.

Another embodiment is advantaged by the fact that cells keep and pass on the ingested semiconductor nanocrystals to their daughter cells, enabling one to track selective deposition of cells on patterned cell adhesion arrays. Cells that have ingested semiconductor nanocrystals are seeded onto the array for patterned cell adhesion or growth. If the desired surface for cell adhesion has been first seeded with semiconductor nanocrystals, confirmation of cell adhesion can be made by a brighter signature luminescence at the loci of desired adhesion. Alternatively, a different colored semiconductor nanocrystal, than the one taken up by the cells, can be seeded onto the array in the desired loci of adhesion. Confirmation of adhesion can be made by observation of cells that have taken up multiple colored semiconductor nanocrystals.

Addition of a dye or a dye linked to biological molecules may be used to label cell features in order to improve the visibility of the engulfed semiconductor nanocrystals. Any dye which is used to highlight cellular structures such as, but not limited to, nucleic acids, proteins, plasma membranes, endoplasmic reticulum, mitochondria and Golgi apparatus, can be used. Examples of appropriate dyes for use in this invention include, but are not limited to, actinomycin D, acridine orange, bisbenzamides such as HOESCHT 33342 (Molecular Probes, Inc., Eugene, Oreg.), Diamidino-2-phenylindole (DAPI), propidium iodide, ethidium bromide, carbocyanines such as JC-1, 3,3'-dihexyloxacarbocyanine iodide (DiO), 1,1'-dioctadecyl-3,3,3',3'-tetramethylindocarbocyanine perchlorate (DiI), pyridinium dibromides such as N-(3-triethylammoniumpropyl)-4-(4-(dibutylamino)styryl) pyridinium dibromide (commercially sold as FM® 1-43, Molecular Probes, Inc.), N-(3-triethylammoniumpropyl)-4-(6-(4(diethylamino)phenyl)hexatrienyl) pyridinium dibromide (commercially sold as FM® 4-64, Molecular Probes, Inc.), and N-(3-trimethylammoniumpropyl)-4-(6-(4(diethylamino)phenyl)hexatrienyl) pyridinium dibromide (commercially sold as FM® 5-95, Molecular Probes, Inc.), Tetramethylrhodamine ethyl ester (TMRE), and ceramides such as NBD C6-Ceramide. Examples of organic fluorescent dyes which are linked to biological molecules that recognize specific cellular structures include but are not limited to a dye such as fluorescein-labeled phalloidin, which binds to and highlights the actin network and specific proteins tagged with complementary fluorescent molecules (for example, GFP, CFP, YFP, or BFP) or other fluorescent dyes.

The lipophilic styryl dye, commercially sold as FM® 4-64, from Molecular Probes, Inc., (Eugene, Oreg.) N-(3-triethylammoniumpropyl)-4-(6-(4(diethylamino)phenyl)hexatrienyl) pyridinium dibromide is preferably used to label cell structures. FM® 4-64 has been reported to selectively stain yeast vacuolar membranes with red fluorescence (excitation/emission maxima ~515/640 nm). One could also use any lipophilic analog of FM® 4-64 with essentially identical spectroscopic properties to label.

(3) Phagokinetic Tracks and Migratory Pathways of Cells 190

Referring now to FIG. 3, depleted regions indicate cell migratory pathways 190 of cells containing semiconductor nanocrystals.

The degree of semiconductor nanocrystal uptake reflects the migratory behavior of the cells. For example, highly dedifferentiated, invasive cancer cells should voraciously engulf semiconductor nanocrystals as they migrate as seen in Example 5. In doing so, the cells generate a region free of semiconductor nanocrystals that clearly reveals their migratory pathways, as can be seen in cells that were cultured on semiconductor nanocrystal-covered collagen for 24 hours (FIGS. 5D-F).

In contrast, non-tumorigenic cells that are not migratory demonstrate an intact layer of semiconductor nanocrystals around them with little or no evidence of motility or migration even after 24 hours of culture on the semiconductor nanocrystal-coated collagen (FIGS. 5J-L). The layer of semiconductor nanocrystals should look virtually identical to that seen around normal cells after three hours of growth on semiconductor nanocrystal-coated collagen (FIGS. 5G-I).

The behavior as seen by the phagokinetic tracks of these two cell types on semiconductor nanocrystal-coated extracellular matrix is consistent with the behaviors characteristically associated with these cell types in the absence of semiconductor nanocrystals-highly-dedifferentiated and invasive cells are migratory and normal non-invasive cells are relatively immotile. Thus, phagokinetic tracking of cells using semiconductor nanocrystals is a distinguishing feature between migratory and immotile cells. Therefore, phagokinetic tracking and cellular imaging using semiconductor nanocrystals can also be used for study of other types of migratory cells as described earlier.

The invention further contemplates using a computing, imaging, detection or measuring means to quantify the area of the depleted regions of semiconductor nanocrystals or the migratory pathways of the cells or by detecting the fluorescence of the nanocrystals in individual cells or a population of cells over a period of time. Illumination of the semiconductor nanocrystals enables a user to measure the amount of semiconductor nanocrystals taken up by at least one cell. This can be done by methods that include, but are not limited to the following: (1) the area of the semiconductor nanocrystal-depleted phagokinetic track left by at least one of one or more cells can be measured; (2) the area of the semiconductor nanocrystal-depleted phagokinetic track left by at least one cell can be compared with a semiconductor nanocrystal-depleted phagokinetic track left by at least one control cell incubated under the same conditions; (3) each cell can be viewed and the vesicles containing the engulfed semiconductor nanocrystals can be imaged.

The comparison of migratory pathways areas or the amount of semiconductor nanocrystals taken up by at least one cell can then be correlated with metabolic properties of the cells in question, including but not limited to, metastatic potential, motility and chemotactic behavior.

EXAMPLE 1

Method of Making Suitable Semiconductor Nanocrystals and Bioconjugation

Briefly, in the first step, hydrophobic CdSe/ZnS nanocrystals are primed with mercaptosilane (mercaptopropyltrimethoxysilane, #175617, Sigma-Aldrich, Milwaukee, Wis., USA) in an alkaline methanol solution. Under these conditions, the mercapto groups bind to the ZnS surface and displace the original surfactant molecules (trioctylphosphineoxide, TOPO, #346187, Sigma-Aldrich). Heating the reaction to 60° C. promotes crosslinking of the methoxy groups and formation of a lattice of siloxane bonds encasing the nanocrystal's core. In the second step, negatively charged phosphonatesilane (trihydroxysilylpropyl methylphosphonate monosodium salt, #435716, Sigma-Aldrich) and mercaptosilane are added and crosslinked to stabilize the nanocrystals in aqueous solution and to introduce surface thiols as functional groups, respectively. In the final step, unreacted methoxy groups were quenched by the addition of chlorotrimethylsilane (#C7,285-4, Sigma-Aldrich) to afford a stable-outer shell.

In order to obtain positively charged or virtually neutral nanocrystals, the phosphonatesilane used in the second step of the silanization was replaced with either polyethylene glycol (PEG)-silane (methoxypolyethyleneoxy propyltrimethoxysilane, #SIM6492.7, Gelest, Tullytown, Pa., USA) or a 1:1 mixture of PEG-silane and ammoniumsilane (trimethoxysilylpropyltrimethylammoniumchloride, #SIT8415.0, Gelest). Since mercaptosilane is used for the first step of the silanization, homogeneous thiol-bearing nanocrystals can be obtained easily. However, if in the second step aminosilane is added, excess mercaptosilane from the first step will result in a mixture of surface amines and thiols. In order to obtain a homogenous amine shell, residual thiol groups are converted to amines by reacting the nanocrystals with iodoethyltrifluoroacetamine (#23010, Pierce, Rockford, Ill., USA) in a post-synthetic manipulation according to the manufacturer's protocol. In a similar manner, nanocrystals with a homogeneous carboxyl surface can be generated by converting the surface thiols to carboxyl groups using maleimidopropionic acid (#394815, Sigma-Aldrich or #22296, Pierce) according to the manufacturer's protocol.

Two procedures have been used for the removal of excess silica. One involves purification of the nanocrystals on an agarose gel, which eliminates most of the small silica nanocrystals and nanocrystal agglomerates (Gerion, D.; Pinaud, F.; Williams, S. C.; Parak, W. J.; Zanchet, D.; Weiss, S.; Alivisatos, A. P. J. Phys. Chem. B 2001, 105:8861-8871). An alternative method utilizes size exclusion chromatography (SEPHADEX G-200 filled columns, #84958, Fluka, Milwaukee, Wis., USA), which also removes small silica nanocrystals and nanocrystal agglomerates. In order to verify removal of excess silane, the number of thiol molecules per nanocrystal in the solution was determined using Ellman's reagent (dithiobisnitrobenzoic acid, #D8130, Sigma-Aldrich or 22582, Pierce) according to the manufacturer's protocol.

Since mercaptosilane is used for the first step of the silanization, homogeneous thiol-bearing nanocrystals can be obtained easily. However, if in the second step aminosilane is added, excess mercaptosilane from the first step will result in a mixture of surface amines and thiols. In order to obtain a homogenous amine shell, residual thiol groups can be converted to amines by reacting the nanocrystals with iodoethyltrifluoroacetamine (#23010, Pierce, Rockford, Ill., USA) in a post-synthetic manipulation according to the manufacturer's protocol. In a similar manner, nanocrystals with a homogeneous carboxyl surface can be generated by converting the surface thiols to carboxyl groups using maleimidopropionic acid (#394815, Sigma-Aldrich or #22296, Pierce).

Thiol-bearing nanocrystals stabilized with PEG or phosphonate were derivitized with amino-modified oligonucleotides in a two-step procedure using the heterobifunctional crosslinker sulfo-SMCC (maleimidomethylcyclohexanecarboxylic acid sulfohydroxysuccinimide ester sodium salt, #M6035, Sigma-Aldrich). Sulfo-SMCC has an N-hydroxysuccinimide (NHS) ester at one end, which reacts with a primary amine to form an amide bond and a maleimide group at the other, which reacts with a thiol to form a thioether. In the first step, the maleimide functional group is introduced into the amino-modified oligonucleotide by condensing the amine of the oligonucleotide with the NHS ester of sulfo-SMCC. In the second step, the maleimide is reacted with a thiol group on the nanocrystal surface to covalently link the oligonucleotide to the particle surface.

Sulfo-SMCC was dissolved in dimethylformamide to approximately 70 mg/ml and added to amino-modified oligonucleotides (21 bases, final DNA concentration about 50 µM, IDT, Coralville, Iowa, USA) in 500-1500 molar excess in 150 mM sodium phosphate buffer, 100-200 mM NaCl, pH 7.0. After incubating for one hour at room temperature, bulk unreacted crosslinker molecules were removed using a SEPHADEX G-25 column (NAP-25, Pharmacia Biotech, Piscataway, N.J., USA). Complete removal of excess crosslinker required two successive purification steps with anion exchange chromatography (1100 Series HPLC system, Agilent, Roseville, Calif., USA) using a Zorbax™ column (Zorbax Bio Series Oligo, analytical column, Du Pont, Wilmington, Del., USA). Eluant fractions containing free crosslinker, unreacted DNA and maleimide-activated DNA could be separated. The latter two fractions were unambiguously identified by MALDI-TOF spectroscopy (data not shown). The eluant fraction containing the maleimide-activated DNA was collected, desalted using a SEPHADEX G-25 column (NAP-25, Pharmacia Biotech, Piscataway, N.J., USA), lyophilized, and stored at −20° C. under nitrogen. Reacting maleimide-activated DNA with thiol groups of mercaptopropionic acid and measuring the increase in mass by MALDI-TOF spectroscopy verified activation.

Maleimide-activated streptavidin and biotin are commercially available and were used without further modification: streptavidin-maleimide (#S9415, Sigma-Aldrich or #31007, Pierce); maleimidopropionylbiocytin (#63183, Fluka) or biotinamido maleimidomethylcyclohexanecarboxamido butane (#21900, Pierce).

Covalent coupling of maleimide-activated oligonucleotides, streptavidin, and biotin to thiol bearing nanocrystals was typically performed in 30-50 mM NaCl in 10-100 mM sodium phosphate buffer, pH 7.3. The ratio of maleimide-bearing biomolecules to thiol-bearing nanocrystals ranged from 0.5 to 500:1, as was the reaction time (several hours to 2 days) at room temperature.

EXAMPLE 2

Making the Semiconductor Nanocrystal Apparatus and Seeding of Cells

Two sizes of semiconductor nanocrystals, CdSe(2.8 nm)/ZnS/SiO$_2$, 8 nm total diameter emitting at 554 nm (red) and CdSe(4.1 nm)/ZnS/SiO$_2$, 16 nm outer diameter emitting at 626 nm (green) were used, as described by D. Gerion et al., Synthesis and Properties of Biocompatible Water-Soluble Silica-Coated CdSe/ZnS Semiconductor Quantum Dots, 105 (37), 8861-8871 *Journal of Physical Chemistry B* (2001) and Example 1. These were negatively charged.

Thin layers of colloidal semiconductor nanocrystals were deposited on collagen-coated tissue culture substrates, followed by seeding of cells. This was done by first adding a collagen solution, such as VITROGEN 100 (2.9 mg/ml Collagen 1 in 12 µM HCl; Cohesion, Palo Alto, Calif., USA) in PBS (1:44), at 4° C., to cell culture/viewing dishes. These were either 35 mm plastic Petri dishes in which the bottom had been replaced with a #1 glass coverslip or in LAB-TEK II chambered coverglass (4 or 8 well). These dishes were stored at 37° C. for 1.5 hours. The excess liquid was then aspirated, green-emitting (8 nm-diameter) or red-emitting (16 nm-diameter) semiconductor nanocrystals were immediately added to the collagen, and the dishes were stored (covered with aluminum foil) in the hood until dry.

Cells were added to the semiconductor nanocrystal-coated viewing dishes at 10,000-20,000 cells/cm$^2$ and stored in the incubator until needed. Two types of cell lines were examined in detail, human mammary epithelial tumor cells MDA-MB-231 (ATCC No. HTB-26, Manassus, Va.) and non-tumor MCF-10A cells (ATTC No. CRL-10317).

EXAMPLE 3

Studying Cellular Uptake of Semiconductor Nanocrystals by Human Mammary Epithelial Tumor Cells (MDA-MB-231) and Non-Tumor Cells (MCF-10A)

As seen in FIG. 4, the semiconductor nanocrystals of Example 1, were readily ingested by all the cell lines examined. Human mammary epithelial tumor cells (MDA-MB-231) were grown on collagen that had been coated with a thin layer of green fluorescent semiconductor nanocrystals as set up in Example 2. A lipophilic styryl dye, FM® 4-64 (#T3166, Molecular Probes, Eugene, Oreg.), frequently used to visualize vacuolar organelles and to study the endocytic pathway, was added to the medium immediately prior to imaging. The FM® 4-64 was rapidly incorporated into the cell plasma membrane, internalized, and packaged in small vesicles (FIG. 4).

As early as three hours after plating of the tumor cells on the green semiconductor nanocrystal-coated collagen, the tumor cells had taken up numerous semiconductor nanocrystals that are packaged in small, but initially separate vesicles, in the cytoplasm. The cells were examined over time by collecting images every 30 seconds using confocal microscopy.

The FM® 4-64 rapidly faded during the first 10 minutes of data collection (one image collected every 20 seconds) due to significant photobleaching, a common characteristic of organic dyes (FIGS. 4A-C). The FM® 4-64 was barely detectable after 5 min and not detectible after 10 min (FIGS. 4D-F). In contrast, the semiconductor nanocrystals demonstrated no photobleaching and actually became brighter upon excitation. Multiple semiconductor nanocrystal-filled vesicles were seen in the cytoplasm. No detectable decrease in the intensity of the green emitting semiconductor nanocrystals was observed during the 16 minutes of imaging shown here (FIGS. 4A-F), or after extended time periods of laser exposure.

EXAMPLE 4

Distinguishing Between Tumor Cells and Non-Tumor Cells Using Confocal Fluorescence Microscopy and Multi-Photon Microscopy The semiconductor nanocrystals of Example 1 are stored in large vesicles after cellular uptake. Human mammary epithelial tumor cells (MDA-MB-231) and non-tumor cells (MCF 10A) were grown on collagen gel, the basic set up as described in Example 2, and coated with either green-emitting (8 nm-diameter) or red-emitting (16 nm-diameter) semiconductor nanocrystals for 24 hours. Optical sections of live cells obtained using a 40×1.3 NA lens determined that the semiconductor nanocrystals are in the cell cytoplasm rather than coating the surface of the cells.

Optical sections obtained with the confocal microscope verified that the semiconductor nanocrystals are within the cell rather than on the inner or outer cell surface (data not shown). A single 0.5 µm thick optical section through the semiconductor nanocrystal-filled vesicles in the MDA-MB-231 cells was obtained using two-photon excitation with a Ti-Sapphire laser, showing small packages of semiconductor nanocrystals on the periphery of the large nanocrystal-filled perinuclear vesicles. These are likely packages of semiconductor nanocrystals prior to incorporation in the large storage vesicles. The large cytoplasmic volume occupied by the semiconductor nanocrystal-filled vesicles becomes quite apparent in the 3D reconstruction of these optical sections.

Non-tumor, relatively immotile cells were observed containing a few small vesicles filled with red-emitting semiconductor nanocrystals. In contrast, the tumor cells were observed to have taken up numerous green-emitting semiconductor nanocrystals that were packaged in large vesicles and stored in the perinuclear region (data not shown). The size of the semiconductor nanocrystals had no influence on the ingestion.

An optical section obtained using two-photon excitation at 760 nm wavelength with a Ti-sapphire laser shows that the semiconductor nanocrystals were not coating the surface of the vesicles; the vesicles are filled with semiconductor nanocrystals. A 3D reconstruction of serial optical sections (not shown) collected with the Ti-Sapphire laser at 0.5 micron intervals revealed the cytoplasmic volume occupied by the massive number of semiconductor nanocrystals taken up by the tumor cells.

After uptake, small vesicles of semiconductor nanocrystals were transported from the cell periphery to the perinuclear region. Transport of one such vesicle was observed as it traveled at 0.1 µm/s towards the nucleus, a velocity compatible with transport via microtubule motors. The growth of cells on a layer of red emitting semiconductor nanocrystals generated identical results (not shown). The size of the semiconductor nanocrystals had no effect on uptake, transport or storage of semiconductor nanocrystals.

Large vesicles of green-emitting semiconductor nanocrystals were seen in the perinuclear region of human mammary epithelial tumor cells (MDA-MB-231) that had been cultured for 7 days. Simultaneous two-photon excitation (760 nm wavelength of a Ti-Sapphire laser) of the DNA label, DAPI, and the green-emitting semiconductor nanocrystals demonstrated that the vesicles are very closely apposed to the nucleus.

EXAMPLE 5

Distinguishing Between Tumor Cells and Non-Tumor Cells using Confocal Fluorescence Microscopy and Multi-Photon Microscopy In this example, human mammary epithelial tumor cells, MDA-MB-231, and non-tumor cells, MCF 10A, were grown on collagen that had been coated with a thin layer of the red 16 nm diameter semiconductor nanocrystals of Example 1, according to the set up as outlined in Example 2. Images were collected with a confocal microscope using fluorescence detectors to examine the semiconductor nanocrystals (FIGS. 5B, 5E, 5H, 5K) and DIC (Differential Interference Contrast) to visualize the cells (FIGS. 5C, 5F, 5I, 5L); the merged images (FIGS. 5A, 5D, 5G, 5J) show the cells and the layer of semiconductor nanocrystals. After 3 hours, the layer of semiconductor nanocrystals beneath the tumor cells (FIG. 5B) and non-tumor cells (FIG. 5H) looks fairly continuous. The cells can only be seen using DIC imaging alone (FIGS. 5C, 5I) or in the merged fluorescent/DIC image (FIGS. 5A, 5G) but not with fluorescence alone (FIGS. 5B, 5H).

The degree of semiconductor nanocrystal uptake reflects the migratory behavior of the cells. MDA-MB-231 cells, which are a highly dedifferentiated, invasive mammary epithelial cancer cell line, voraciously engulf semiconductor nanocrystals as they migrate. In doing so, they generate a region free of semiconductor nanocrystals that clearly reveals their migratory pathways, as can be seen in cells that were cultured on semiconductor nanocrystal-covered collagen for 24 hours (FIGS. 5D-F). Such clearings are not seen around cells examined three hours after plating (FIGS. 5A-C). The semiconductor nanocrystal-free zone around the MDA-MB-231 cells seen after 24 hours is created by the uptake of the semiconductor nanocrystals as the cells crawl around the dish, rather than the displacement or degradation of semiconductor nanocrystals. When optical sections of the cells were obtained using confocal microscopy, numerous large vesicles filled with semiconductor nanocrystals were seen juxtaposed to the nucleus in the MDA-MB-231 tumor cells after 24 hours, whereas only a few, small foci containing semiconductor nanocrystals can be seen in the MCF-10A cells.

In contrast, the MCF-10A cells, a highly differentiated, spontaneously immortalized, non-tumor mammary epithelial cell line that is not migratory, demonstrate an intact layer of semiconductor nanocrystals around them with little or no evidence of motility or migration after 24 hours of culture on the semiconductor nanocrystal-coated collagen (FIGS. 5J-L). The layer of semiconductor nanocrystals looks virtually identical to that seen around cells after three hours of growth on the semiconductor nanocrystal-coated collagen (FIGS. 5G-I). The behavior of these two cell types on semiconductor nanocrystal-coated extracellular matrix is consistent with the behaviors characteristically associated with these cell types in the absence of semiconductor nanocrystals; MDA-MB-231 cells are very invasive and migratory and MCF-10A cells are non-invasive, relatively immotile cells.

After 24 hours large clearings in the semiconductor nanocrystals layer are observed around the tumor cells (FIGS. 5D, 5E), but not the non-tumor cells (FIGS. 5J, 5K). The semiconductor nanocrystal-filled tumor cells are also fluorescing brightly after 24 hours (FIG. 5E). The non-tumor cells, in contrast, seen in DIC (FIG. 5L) cannot be detected with the fluorescent detector after 24 hours (FIG. 5K). The images were collected at the optical section that best showed the layer of semiconductor nanocrystals. Since some tumor cells are crawling into the underlying collagen after 24 hours, they are less distinct in the DIC image (FIG. 5F). FIGS. 5A-5C are a composite of several small images of adjacent regions on the dish. The arc of brighter fluorescence is due to photo brightening caused by illumination of that region to the mercury arc lamp.

EXAMPLE 6

Making Mixed Co-Cultures of Cells and Tracking Cell Lineage

MCF-10A cell (normal mammary epithelial) and MDA-MB-231 cells (mammary epithelial tumor cells) were purchased from the American Type Culture Collection (http://www.atcc.org).

On Day 1, 0.1 to $0.15 \times 10^6$ cells were plated in 1.5 cm well on plastic and grown in appropriate media in 37° C. incubator overnight. On Day 2, the media was removed and 110 μmol red 16 nm diameter semiconductor nanocrystals in 110 μl water were added to wells containing MCF-10a cells and incubated at room temperature while rocking for 30 minutes. The media was removed and 110 μmol green 8 nm diameter semiconductor nanocrystals in 110 μl water were added to wells containing MDA-MB-231 cells and incubated at room temperature while rocking for 30 minutes. Appropriate media was added back and replaced in 37° C. incubator overnight to allow cells to recover.

On Day 3, 4-well chambered coverglass was coated with 70 μl (or 8-well chambered coverglass with 35 μl) growth factor reduced BD MATRIGEL™ Matrix. The coverglass was placed in incubator to polymerize. The cells that had taken up the semiconductor nanocrystals from the 1.5 cm well were then trypsinized (trypsin obtained from GIBCO, Invitrogen, Carlsbad, Calif.). The cells were pelleted and the supernatant was aspirated.

For co-cultures to be viewed in 24 hours, 1.1 ml mammary epithelial basal medium (MEBM) (Clonetics Corp., San Diego, Calif.) supplemented with 10% fetal bovine serum was added to pellets then 400 μl of both cell types per well (1:1 ratio) were plated. The following ratios also worked when added 970 μl to pellets: 180 μl MCF 10A cells with 360 μl MDA-MB-231 cells (1:4 ratio), 180 μl MCF 10A cells with 180 μl MDA-MB-231 cells (1:1 ratio), 180 μl MCF 10A cells with 90 μl MDA-MB-231 cells (2:1 ratio), 180 μl MCF 10A cells with 45 μl MDA-MB-231 cells (4:1 ratio).

For co-cultures to be viewed in 4 to 10 days, add 1.1 ml MEBM supplemented with 0.4% Bovine pituitary extract, 0.01 μg/ml human epidermal growth factor, 5 μg/ml insulin, and 0.5 μg/ml hydrocortisone to MCF 10A pellets then plate 50 μl of to 300 μl per well. Once colonies begin to form, MDA-MB-231 cells were plated into 1.5 cm wells on plastic and treated with semiconductor nanocrystals as described above. On Day 3, MDA-MB-231 semiconductor nanocrystal-labeled cells were pelleted, 1.1 ml MEBM supplemented with 10% fetal bovine serum was added to pellet, and 50 μl or 300 μl was added to established doped MCF 10A colonies on top of Matrigel.

The color photograph in FIG. 6 shows the mixed colonies formed by MCF 10A cells when co-cultured with MDA-MB-231 cells. The normal mammary epithelial MCF-10A cells are labeled in red, while the mammary epithelial tumorigenic MDA-MD-231 cells are labeled in green.

The present examples, methods, procedures, treatments, cell types, specific compounds and molecules are meant to exemplify and illustrate the invention and should in no way be seen as limiting the scope of the invention. Various modifications and variations of the described method and apparatus of the invention will be apparent to those skilled in the art without departing from the scope and spirit of then invention.

Any patents or publications mentioned in this specification are indicative of levels of those skilled in the art to which the paten pertains and are hereby reference to the same extent as if each was specifically and individually incorporated by reference.

What is claimed is:

1. A method for phagokinetic tracking, comprising:
providing a culture surface for supporting biological activity of living cells;
depositing semiconductor nanocrystals on the culture surface, thereby resulting in deposited semiconductor nanocrystals;
noting the starting positions of the deposited semiconductor nanocrystals on the culture surface;
seeding the cells onto the culture surface;
allowing the seeded cells to move and take up the deposited semiconductor nanocrystals; and
detecting a phagokinetic track of the cells by observing changes in the positions of the deposited semiconductor nanocrystals after sufficient time has elapsed to allow the seeded cells to move and take up the deposited semiconductor nanocrystals, wherein the changes in the positions of the deposited semiconductor nanocrystals indicate the phagokinetic track of the cell and wherein the detection of a phagokinetic track of the cells indicates the cells having the properties of motility, migration, movement and/or metastatic potential.

2. The method of claim 1 further comprising adding a marker to be taken up by the cells, wherein the marker is selected from the group consisting of other semiconductor nanocrystals that are different from the deposited semiconductor nanocrystals and an organic fluorescent dye.

3. The method of claim 2 wherein the organic fluorescent dye is selected from the group consisting of actinomycin D, acridine orange, bisbenzimide, 4',6-Diamidino-2-phenylindole (DAPI), propidium iodide, ethidium bromide, carbocyanines, pyridinium dibromides, tetramethylrhodamine ethyl ester (TMRE), ceramides, fluorescein-labeled phalloidin, GFP, DsRed, YCP, CFP and BFP.

4. The method of claim 1 wherein the detecting-takes place over a time period between ten minutes and 10 days.

5. The method of claim 1 wherein each of the semiconductor nanocrystals comprises a core semiconductor covered by a hydrophilic outermost shell.

6. The method of claim 5 wherein the core is CdSe.

7. The method of claim 6 wherein the outermost shell is a siloxane.

8. The method of claim 7 wherein each of the semiconductor nanocrystals further comprises an intermediate shell of ZnS.

9. The method of claim 5 wherein the outermost shell comprises a stabilizing group which carries a positive charge.

10. The method of claim 1 further comprising adding other semiconductor nanocrystals that have a different size from the deposited semiconductor nanocrystals.

11. The method of claim 1 wherein the depositing comprises depositing the semiconductor nanocrystals in patterned arrangements onto the culture surface.

12. The method of claim 1 wherein the depositing comprises depositing the semiconductor nanocrystals in linear arrangements onto the culture surface.

13. The method of claim 1 wherein the depositing comprises depositing the semiconductor nanocrystals homogenously onto the culture surface.

14. The method of claim 1 wherein the culture surface comprises an extracellular matrix.

15. The method of claim 14 wherein the extracellular matrix comprises proteins.

16. The method of claim 15 wherein the proteins are selected from the group consisting of collagen, laminin, fibronectin, elastin, nidogen, enactin, and proteoglycan.

17. The method of claim 1 wherein the cells are cancerous.

18. The method of claim 1 wherein the cell properties are correlated with metastatic potential.

19. The method of claim 1 further comprising measuring or quantifying cell motility.

20. The method of claim 1 further comprising measuring or quantifying cell chemotactic behavior.

21. The method of claim 7 wherein each of the semiconductor nanocrystals further comprises an intermediate shell of CdS.

22. The method of claim 5 wherein the outermost shell comprises a stabilizing group which carries a negative charge.

* * * * *